US008722966B2

(12) United States Patent
Sela et al.

(10) Patent No.: US 8,722,966 B2
(45) Date of Patent: May 13, 2014

(54) PLANT EXPRESSION CONSTRUCTS COMPRISING AND USES THEREOF

(75) Inventors: Ilan Sela, Ramot-HaShavim (IL); Yuval Peretz, Rechovot (IL); Rita Mozes-Koch, Yavne (IL)

(73) Assignees: Yissum Research Development Company of the Hebrew University of Jerusalem Ltd., Jerusalem (IL); Morflora Israel Ltd., Moshav Sharsheret (IL)

( * ) Notice: Subject to any disclaimer, the term of this patent is extended or adjusted under 35 U.S.C. 154(b) by 106 days.

(21) Appl. No.: 13/003,151

(22) PCT Filed: Jul. 8, 2009

(86) PCT No.: PCT/IL2009/000682
§ 371 (c)(1),
(2), (4) Date: Feb. 23, 2011

(87) PCT Pub. No.: WO2010/004561
PCT Pub. Date: Jan. 14, 2010

(65) Prior Publication Data
US 2011/0162106 A1 Jun. 30, 2011

Related U.S. Application Data

(60) Provisional application No. 61/129,596, filed on Jul. 8, 2008.

(51) Int. Cl.
*C07K 14/415* (2006.01)
*A01H 5/06* (2006.01)
*C12N 15/86* (2006.01)

(52) U.S. Cl.
USPC ........... 800/278; 800/280; 800/285; 800/286; 800/279; 800/317; 435/91.42; 435/91.4; 435/320.1

(58) Field of Classification Search
None
See application file for complete search history.

(56) References Cited

U.S. PATENT DOCUMENTS

| 5,981,236 | A | 11/1999 | Kridl et al. | |
| 6,147,278 | A * | 11/2000 | Rogers et al. | 800/278 |
| 6,392,121 | B1 * | 5/2002 | Mason et al. | 800/287 |
| 2003/0079248 | A1 | 4/2003 | Mason et al. | |
| 2010/0071088 | A1 | 3/2010 | Sela et al. | |

FOREIGN PATENT DOCUMENTS

| CN | 1425772 A * | 6/2003 |
| WO | WO 99/50429 | 10/1999 |
| WO | WO 00/20557 | 4/2000 |
| WO | WO 01/94604 | 12/2001 |
| WO | WO 2007/141790 | 12/2007 |
| WO | WO 2010/004561 | 1/2010 |

OTHER PUBLICATIONS

Varsani et al. (Virol. J. (2009) 6: 36).*
Guo et al. (PNAS (2004) 101: 9205-9210).*
Van Wezel et al. (MPMI vol. 14, No. 9, 2001, pp. 1125-1128.).*
Settlage et al. (Journal of Virology, Aug. 2005, p. 9885-9895).*
Official Action Dated Nov. 8, 2011 From the US Patent and Trademark Office Re. U.S. Appl. No. 12/308,121.
Andret-Link et al. "Transmission Specificity of Plant Viruses by Vectors", Journal of Plant Pathology, 87(3): 153-165, 2005.
Gleba et al. "Engineering Viral Expression Vectors for Plants: The 'Full Virus' and the 'Deconstructed Virus' Strategies", Current Opinion in Plant Biology, 7: 182-188, 2004.
Guo et al. "Protein Tolerance to Random Amino Acid Change", Prioc. Natl. Acad. Sci. USA, PNAS, 101(25): 9205-9210, Jun. 22, 2004.
Hamilton et al. "Tomato Golden Mosaic Virus DNA-A, Complete Sequence", NCBI GenBank, Accession No. NC_001507.1, 2002.
Hayes et al. "Stability and Expression of Bacterial Genes in Replicating Geminivirus Vectors in Plants", Nucleic Acids Research, 17(7): 2391-2403, 1989.
Orozco et al. "Functional Domains of A Geminivirus Replication Protein", The Journal of Biological Chemistry, 272(15): 9840-9846, Apr. 11, 1997.
Rigden et al. "Plant Virus DNA Replication Processes in Agrobacterium: Insight Into the Origins of Geminiviruses?", Proc. Natl. Acad. Sci. USA 93: 10280-10284, Sep. 1996.
Varsani et al. "A Highly Divergent South African Geminivirus Species Illuminates the Ancient Evolutionary History of this Family", Virology Journal, 6(36): 1-12, Mar. 25, 2009.
Response Dated Sep. 27, 2011 to Communication Pursuant to Article 94(3) EPC of May 19, 2011 From the European Patent Office Re.: Application No. 07736428.9.
Examination Report Dated Feb. 21, 2012 From the Instituto Mexicano de la Propriedad Industrial Re. Application No. MX/a/2011/000214 and Its Summary in English.
European Search Report and the European Search Opinion Dated Mar. 1, 2012 From the European Patent Office Re. Application No. 11009695.5.

(Continued)

*Primary Examiner* — David T Fox
*Assistant Examiner* — Jared Shapiro

(57) ABSTRACT

Methods of expressing a molecule of interest in a plant are disclosed. One method comprises contacting roots of the plant in a solution comprising at least one Geminivirus based expression construct so as to allow the at least one Geminivirus based expression construct to be absorbed by the roots, the expression construct comprising a polynucleotide encoding the molecule of interest, and further the expression construct being capable of systemic symptomless spread in a plant host, thereby expressing a molecule of interest in a plant. Expression constructs capable of systemic symptomless spread in a host plant are also disclosed.

19 Claims, 6 Drawing Sheets

(56) References Cited

OTHER PUBLICATIONS

Official Action Dated Apr. 25, 2012 From the US Patent and Trademark Office Re. U.S. Appl. No. 12/308,121.
Search Report and Written Opinion Dated Apr. 18, 2012 From the Intellectual Property Office of Singapore Issued by the Danish Patent and Trademark Office on Mar. 15, 2012 Re. Application No. 201100063-5.
Communication Pursuant to Rules 70(2) and 70a(2) EPC and Reference to Rule 39(1) EPC Dated Apr. 11, 2012 From the European Patent Office Re. Application No. 11009695.5.
Translation of Office Action Dated May 3, 2012 From the State Intellectual Property Office of the People's Republic of China Re. Application No. 200980129925.3.
Communication Pursuant to Article 94(3) EPC Dated Jun. 11, 2012 From the European Patent Office Re.: Application No. 07736428.9.
Examination Report Dated Jun. 12, 2012 From the Instituto Mexicano de la Propiedad Industrial Re. Application No. MX/a/2011/000214 and Its Summary in English.
Communication Pursuant to Article 94(3) EPC Dated Dec. 8, 2009 From the European Patent Office Re.: Application No. 07736428.9.
Communication Pursuant to Article 94(3) EPC Dated Aug. 10, 2010 From the European Patent Office Re.: Application No. 07736428.9.
Communication Pursuant to Article 94(3) EPC Dated May 19, 2011 From the European Patent Office Re.: Application No. 07736428.9.
International Preliminary Report on Patentability Dated Dec. 10, 2008 From the International Bureau of WIPO Re.: Application No. PCT/IL2007/000688.
International Preliminary Report on Patentability Dated Jan. 20, 2011 From the International Bureau of WIPO Re. Application No. PCT/IL2009/000682.
International Search Report and the Written Opinion Dated Jan. 17, 2008 From the International Searching Authority Re.: Application No. PCT/IL2007/000688.
International Search Report and the Written Opinion Dated Oct. 27, 2009 From the International Searching Authority Re.: Application No. PCT/IL2009/000682.
Official Action Dated Jul. 20, 2011 From the US Patent and Trademark Office Re. U.S. Appl. No. 12/308,121.
Response Dated May 3, 2010 to Communication Pursuant to Article 94(3) EPC of Dec. 8, 2009 From the European Patent Office Re.: Application No. 07736428.9.
Response Dated Feb. 18, 2011 to Communication Pursuant to Article 94(3) EPC of Aug. 10, 2010 From the European Patent Office Re.: Application No. 07736428.9.
Response Dated Sep. 20, 2011 to Communication Pursuant to Article 94(3) EPC of May 19, 2011 From the European Patent Office Re.: Application No. 07736428.9.
Response Dated Sep. 20, 2011 to Official Action of Jul. 20, 2011 From the US Patent and Trademark Office Re. U.S. Appl. No. 12/308,121.
Atkinson et al. "Post-Transcriptional Silencing of Chalcone Synthase in Petunia Using a Geminivirus-Based Episomal Vector", The Plant Journal, 15(5): 593-604, 1998.
Behjatnia et al. "Identification of the Replication-Associated Protein Binding Domain Within the Intergenic Region of Tomato Leaf Curl Geminivirus", Nucleic Acids Research, 26(4): 925-931, 1998.
Beisson et al. "Begomovirus", Sixth ICTV Report, rf_gemini.htm.
Czosnek et al. "Tomato Yellow Leaf Curl Virus, A Geminivirus With a Single Genomic Component: Molecular Analysis of Infection and New Ways for Tomato Protection", Acta Horiculturae, XP009123949, 377: 251-257, Oct. 1, 1994. p. 253, § 6, p. 255, § 3.
Hong et al. "Novel System for the Simultaneous Analysis of Geminivirus DNA Replication and Plant Interactions in *Nicotiana benthamiana*", Journal of Virology, 77(24): 13315-13322, 2003.
Kasrawi et al. "Sources of Resistance to Tomato-Yellow-Leaf-Curl-Virus (TYLCV) in *Lycopersicon* Species", Euphytica, XP009124008, 37(1): 61-64, Jan. 1, 1988. p. 62, col. 2, § 2.

Lapidot "Screeing for TYLCV-Resistant Plants Using Whitefly-Mediated Inoculation", Tomato Yellow Leaf Curl Virus Disease: Management, Molecular Biology, Breeding for Resistance, XP009124014, p. 329-342, Jan. 1, 2007. p. 334, § 3.
Mor et al. "Geminivirus Vectors for High-Level Expression of Foreign Proteins in Plant Cells", Biotechnology and Bioengineering, 81(4): 430-437, 2003.
Morilla et al. "A Versatile Transreplication-Based System to Identify Cellular Proteins Involved in Geminivirus Replication", Journal of Virology, 80(7): 3624-3633, 2006.
Noris et al. "Resistance to Tomato Yellow Leaf Curl Geminivirus in *Nicotiana benthamiana* Plants Transformed With a Truncated Viral C1 Gene", Virology, 224: 130-138, 1996.
Padidam et al. "The Role of AV2 (Precoat) and Coat Protein in Viral Replication and Movement in Tomato Leaf Curl Geminivirus", Virology, 224: 390-404, 1996.
Peretz et al. "A Universal Expression/Silencing Vector in Plants [C][OA]", Plant Physiology, XP002550013, 145(4): 1251-1263, Dec. 2007. Abstract.
Petty et al. "Complementable and Noncomplementable Host Adaption Defects in Bipartite Geminiviruses", Virology, XP002550014, 212(1): 263-267, 1995. p. 263, col. 2, § 2.
Shadwick et al. "Infection, Propagation, Distribution and Stability of Plant Virus in Hairy Root Cultures", Journal of Biotechnology, XP022232036, 131(3): 318-329, Sep. 6, 2007.
Tamilselvi et al. "A Geminivirus AYVV-Derived Shuttle Vector for Tobacco BY2 Cells", Plant Cell Reports, XP002550015, 23(1-2): 81-90, Aug. 2004.
Search Report Dated Oct. 10, 2012 From the Danish Patent Office on Behalf of the Intellectual Property Office of Singapore Re. Application No. 201100063-5.
Communication Pursuant to Article 94(3) EPC Dated Feb. 19, 2013 From the European Patent Office Re. Application No. 09787461.4.
Translation of Office Action Dated Feb. 20, 2013 From the State Intellectual Property Office of the People's Republic of China Re. Application No. 200980129925.3.
Request for Examination Dated May 7, 2013 From the Patent Office of the Russian Federation (ROSPATENT), Federal Institute of Industrial Property Re. Application No. 2011103072 and Its Translation Into English.
Communication Pursuant to Article 94(3) EPC Dated Jan. 3, 2013 From the European Patent Office Re. Application No. 11009695.5.
Communication under Rule 71(3) EPC Dated May 29, 2013 From the European Patent Office Re.: Application No. 07736428.9.
Preliminary Decision on Refusal Dated Jul. 3, 2013 From the State Intellectual Property Service of Ukraine, State Enterprise 'Ukrainian Institute for Industrial Property' Re. Application No. 201100882 and Its Translation Into English.
Communication Pursuant to Article 94(3) EPC Dated Aug. 1, 2013 From the European Patent Office Re. Application No. 11009695.5.
Communication Pursuant to Article 94(3) EPC Dated Dec. 4, 2013 From the European Patent Office Re. Application No. 09787461.4.
Communication Under Rule 71(3) EPC Dated Nov. 6, 2013 From the European Patent Office Re. Application No. 07736428.9.
Office Action Dated Sep. 30, 2013 From the State Intellectual Property Office of the People's Republic of China Re. Application No. 200980129925.3 and Its Translation Into English.
Inquiry of the State Examination Dated Nov. 28, 2013 From the Patent Office of the Russian Federation (ROSPATENT), Federal Institute of Industrial Property Re. Application No. 2011103072 and Its Translation Into English.
Requirement for Additional Materials Dated Jan. 19, 2014 From the State Intellectual Property Service of Ukraine, State Enterprise 'Ukrainian Institute for Industrial Property' Re. Application No. 201100882 and Its Translation Into English.
Communication Pursuant to Article 94(3) EPC Dated Feb. 17, 2014 From the European Patent Office Re. Application No. 11009695.5.

* cited by examiner

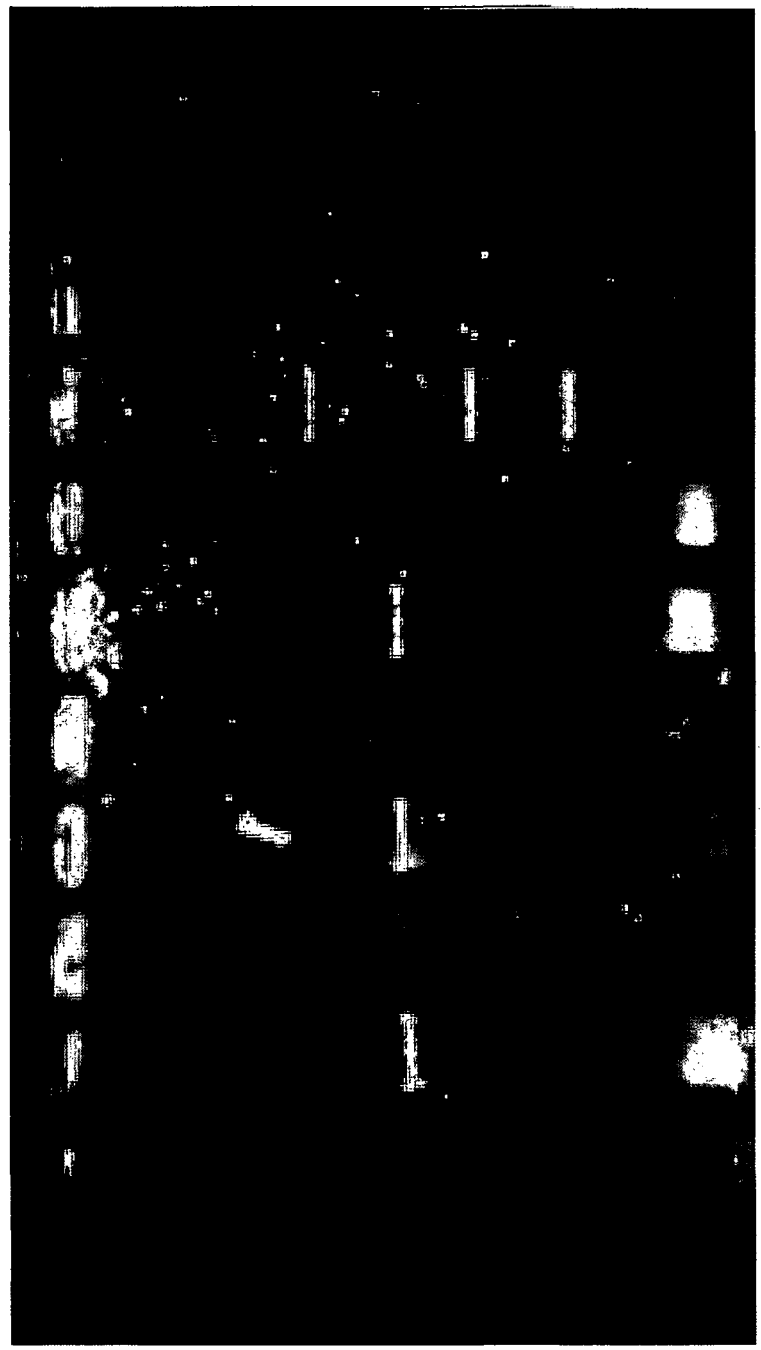

ND USES THEREOF

SEQUENCE LISTING

```
<160> NUMBER OF SEQ ID NOS: 38

<210> SEQ ID NO 1
<211> LENGTH: 5509
<212> TYPE: DNA
<213> ORGANISM: Artificial sequence
<220> FEATURE:
<223> OTHER INFORMATION: IL-60-BS polynucleotide

<400> SEQUENCE: 1
gttgaaatga atcggtgtct ctcaaagctc tatggcaatc ggtgtatcgg tgtcttactt      60
atacctggac acctaatggc tatttggtaa tttcataaat gttcattgca attcaaaatt     120
caaaattcaa aaatcaaatc tttaaagcgg ccatccgtat aatattaccg gatggccgcg     180 cctttttgttt ttatgtggtc cccacgaggg ttacacagac gtcactgtca accaatcaaa    240
ttgcattctc aaacgttaga taagtgttca tttgtcttta tatacttggt ccccaagttt    300
tttgtcttgc aatatgtggg acccacttct taatgaattt cctgaatctg ttcacggatt    360
tcgttgtatg ttagctatta aatatttgca gtccgttgag gaaacttacg agcccaatac    420
attgggccac gatttaatta gggatcttat atctgttgta agggccccgt gactatgtcg    480
aagcgaccag gcgatataat catttccacg cccgtctcga aggttcgccg aaggctgaac    540
ttcgacggcc catacaggcc catgtaccga aagcccagaa atacagaatg tatcgaagcc    600
ctgatgttcc ccgtggatgt gaaggcccct ttaaagtcca gtcttatgag caacgggatg    660
atattaagca tcctggtatt gttcggttgt gttagtgatg ttactcgtgg atctggaatt    720
actcacagag tgggtaagag gttctgtgtt aaatcgatat attttttagg taaagtctgg    780
atggatgaaa atatcaagaa gcagaatcac actaatcagg tcatgttctt cttggtccgt    840
```

```
gatagaaggc cctatggaaa cagcccaatg gattttggac aggttttaa tatgttcgat    900 aatgagccca gtaccgcaac cgtgaagaat gatttgcgtg ataggtttca agtgatgagg    960
aaatttcatg ctacagttat tggtgggccc tctggaatga aggaacaggc attagttaag   1020
agatttttta aaattaacag tcatgtaact tataatcatc aggaggcagc aaagtacgag   1080
aaccatactg aaaacgcctt gttattgtat atggcatgta cgcatgcctc taatccagtg   1140
tatgcaacta tgaaaatacg catctatttc tatgattcaa tatcaaatta ataaaattta   1200
tattttatat catgagtttc tgttacattt attgtgtttt caagtacatc atacaataca   1260
tgatcaactg ctctgattac attgttaatg gaaattacac caagactatc taaatactta   1320
agaacttcat atctaaatac tcttaagaaa tgaccagtct gaggctgtaa tgtcgtccaa   1380
attcggaagt tgagaaaaca tttgtgaatc cccattacct tcctgatgtt gtggttgaat   1440
cttatctgaa tggaaatgat gtcgtggttc attagaaatg gcctctggct gtgttctgtt   1500
atcttgaaat agaggggggat tgttatctcc cagataaaaa cgccattctc tgcctgagga   1560
gcagtgatga gttcccctgt gcgtgaatcc atgattattg cagttgaggt ggaggtagta   1620
tgagcagcca cagtctaggt ctacacgctt acgccttatt ggtttcttct tggctatctt   1680
gtgttggacc ttgattgata cttgcgaaca gtggctcgta gagggtgacg aaggttgcat   1740
tcttgagagc ccaattttc aaggatatgt ttttttcttc gtctagatat tcctatatg    1800 atgaggtagg tcctggattg cagaggaaga tagtgggaat tcccccttta atttgaatgg   1860
gcttcccgta ctttgtgttg ctttgccagt ccctctgggc ccccatgaat tccttgaagt   1920
gctttaaata atgcgggtct acgtcatcaa tgacgttgta ccacgcatca ttactgtaca   1980
cctttgggct taggtctaga tgtccacata aataattatg tgggcctaga gacctggccc   2040
acattgtttt gcctgttctg ctatcaccct caatgacaat acttatgggt ctccatggcc   2100
gcgcagcgga atacacgacg ttctcggcga cccactcttc aagttcatct ggaacttgat   2160
taaaagaaga agaaagaaat ggagaaacat aaacttctaa aggaggacta aaaatcctat   2220
ctaaatttga acttaaatta tgaaattgta aaatatagtc ctttggggcc ttctcttta    2280 atatattgag ggcctcggat ttactgcctg aattgagtgc ttcggcatat gcgtcgttgg   2340
cagattgctg acctcctcta gctgatctgc catcgatttg gaaaactcca aaatcaatga   2400
agtctccgtc tttctccacg taggtcttga catctgttga gctcttagct gcctgaatgt   2460
tcggatggaa atgtgctgac ctgtttgggg ataccaagtc gaagaaccgt tggttcttac   2520
attggtattt gccttcgaat tggataagca catggagatg tggttcccca ttctcgtgga   2580
gttctttgca aactttgatg tattttttat ttgttggggt ttctagtttt tttaattggg   2640
aaagtgcttc ctctttagag agagaacaat tgggatatgt taggaaataa tttttggcat   2700
atattttaaa taaacgaggc atgttgaaat gaatcggtgt ccctcaaagc tctatggcaa   2760
tcggtgtatc ggtgtcttac ttatacttgg acacctaatg gctatttggt aatttcataa   2820
atgttcattt caattcaaaa ttcaaaattc aaaaatcaaa tcattaaagc ggccatccgt   2880
ataatattac cggatggccg cgccttttcc ttttatgtgg tccccacgag ggttacacag   2940
atgttattgt caaccaatca aattgcattc tcaaacgtta gataagtgtt catttgtctt   3000
tatatacttg gtccccaagt ttttgtctt gcaatatgtg ggacccactt cttaatgaat    3060
ttcctgaatc tgttcacgga tttcgttgta tgttagctat taaatatttg cagtccgttg   3120
aggaaactta cgagcccaat acattgggcc acgatttaat tagggatctt atatctgttg   3180
taagggcccg tgactatgtc gaagcgacca ggcgatataa tcatttccac gcccgtctcg   3240
```

```
aaggttcgcc gaaggctgaa cttcgacagc ccatacagca gccgtgctgc tgtccccatt    3300
gtccaaggca caaacaagcg acgatcatgg acgtacaggc ccatgtaccg aaagcccaga    3360
atatacagaa tgtatcgaag ccctgatgtt ccccgtggat gtgaaggccc atgtaaagtc    3420
cagtcttatg agcaacggga tgatattaag catactggta ttgttcgttg tgttagtgat    3480
gttactcgtg gatctggaat tactcacaga gtgggtaaga ggttctgtgt taaatcgata    3540
tatttttag gtaaagtctg gatggatgaa aatatcaaga agcagaatca cactaatcag    3600
gtcatgttct tcttggtccg tgatagaagg ccctatggaa acagcccaat ggattttgga    3660
caggttttta atatgttcga taatgagccc agtaccgcaa ccgtgaagaa tgatttgcgt    3720
gataggtttc aagtgatgag gaaatttcat gctacagtta ttggtgggcc ctctggaatg    3780
aaggaacagg cattagttaa gagatttttt aaaattaaca gtcatgtaac tttatttata    3840
ttcattcagg aggcagcaaa gtacgagaac catactgaaa acgccttgtt attgtatatg    3900
gcatgtacgc atgcctctaa tccagtgtat gcaactatga aaatacgcat ctatttctat    3960
gattcaatat caaattaata aaatttatat tttatatcat gagtttctgt tacatttatt    4020
gtgttttcaa gtacatcata caatacatga tcaactgctc tgattacatt gttaatggaa    4080
attacaccaa gactatctaa atacttaaga acttcatatc taaatactct taagaaatga    4140
ccagtctgag gctgtaatgt cgtccaaatt cggaagtcga gaaacatttt gtgaatcccc    4200
attccttcc tgatgttgtg gttgaatctt atctgaatgg aaatgatgtc gtggttcatt    4260
agaaatggcc tctggctgtg ttctgttatc ttgaaataga ggggattgtt tatctcccag    4320
ataaaaacgc cattctctgc ctgaggagca gtgatgagtt cccctgtgcg tgaatccatg    4380
attattgcag ttgaggtgga ggtagtatga gcagccacag tctaggtcta cacgcttacg    4440
ccttattggt ttcttcttgg ctatcttgtg ttggaccttg attgatactt gcgaacagtg    4500
gctcgtagag ggtgacgaag gttgcattct tgagagccca atttttcaag gatatgtttt    4560
tttcttcgtc tagatattcc ctatatgagg aggtaggtcc tggattgcag aggaagatag    4620
tgggaattcc ccctttaatt tgaatgggct tcccgtactt tgtgttgctt tgccagtccc    4680
tctgggcccc catgaattcc ttgaagtgct ttaaataatg cgggtctacg tcatcaatga    4740
cgttgtacca cgcatcatta ctgtacacct ttgggcttag gtctagatgt ccacataaat    4800
aattatgtgg gcctagagac ctggcccaca ttgttttgcc tgttctgcta tcaccctcaa    4860
tgacaatact tatgggtctc catggccgcg cagcggaata cacgacgttc tcggcgaccc    4920
actcttcaag ttcatctgga acttgattaa agaagaagaa aagaaatgga gaaacataaa    4980
cttctaaagg aggactaaaa atcctatcta aatttgaact taaattatga aattgtaaaa    5040
tatagtcctt tggggccttc tcttttaata tattgagggc ctcggattta ctgcctgaat    5100
tgagtgcttc ggcatatgcg tcgttggcag attgctgacc tcctctagct gatctgccat    5160
cgatttggga aactccaaaa tcaatgaagt ttccgtcttt ctccacgtag gtcttgacat    5220
ctgttgagct cttagctgcc tgaatgttcg gatggaaatg tgctgacctg tttggtgata    5280
ccaggtcgaa gaaccgttgg ttcttacatt ggtatttgcc ttcgaattgg ataagcacat    5340
ggagatgtgg ttccccattc tcgtggagtt ctctgcaaac tttgatgtat tttttatttg    5400
ttggggtttc taggtttttt aattgggaaa gtgcttcctc tttagagaga gaacaattgg    5460
gatatgttag gaaataattt ttggcatata ttttaaataa acgaggcat              5509
```

<210> SEQ ID NO 2
<211> LENGTH: 2722
<212> TYPE: DNA

<213> ORGANISM: Artificial sequence
<220> FEATURE:
<223> OTHER INFORMATION: IL-60 polynucleotide

<400> SEQUENCE: 2

```
gttgaaatga atcggtgtct ctcaaagctc tatggcaatc ggtgtatcgg tgtcttactt      60
atacctggac acctaatggc tatttggtaa tttcataaat gttcattgca attcaaaatt     120
caaaattcaa aaatcaaatc tttaaagcgg ccatccgtat aatattaccg gatggccgcg     180
ccttttgttt ttatgtggtc cccacgaggg ttacacagac gtcactgtca accaatcaaa     240
ttgcattctc aaacgttaga taagtgttca tttgtcttta tatacttggt ccccaagttt     300
tttgtcttgc aatatgtggg acccacttct taatgaattt cctgaatctg ttcacggatt     360
tcgttgtatg ttagctatta aatatttgca gtccgttgag gaaacttacg agcccaatac     420
attgggccac gatttaatta gggatcttat atctgttgta agggcccccgt gactatgtcg     480
aagcgaccag gcgatataat catttccacg cccgtctcga aggttcgccg aaggctgaac     540
ttcgacggcc catacaggcc catgtaccga agcccagaa atacagaatg tatcgaagcc     600
ctgatgttcc ccgtggatgt gaaggccccct taaagtcca gtcttatgag caacgggatg     660
atattaagca tcctggtatt gttcggttgt gttagtgatg ttactcgtgg atctggaatt     720
actcacagag tgggtaagag gttctgtgtt aaatcgatat attttttagg taaagtctgg     780
atggatgaaa atatcaagaa gcagaatcac actaatcagg tcatgttctt cttggtccgt     840
gatagaaggc cctatggaaa cagcccaatg gattttggac aggtttttaa tatgttcgat     900
aatgagccca gtaccgcaac cgtgaagaat gatttgcgtg ataggtttca agtgatgagg     960
aaatttcatg ctacagttat tggtgggccc tctggaatga aggaacaggc attagttaag    1020
agatttttta aaattaacag tcatgtaact tataatcatc aggaggcagc aaagtacgag    1080
aaccatactg aaaacgcctt gttattgtat atggcatgta cgcatgcctc taatccagtg    1140
tatgcaacta tgaaaatacg catctatttc tatgattcaa tatcaaatta ataaaattta    1200
tattttatat catgagtttc tgttacattt attgtgtttt caagtacatc atacaataca    1260
tgatcaactg ctctgattac attgttaatg gaaattacac caagactatc taaatactta    1320
agaacttcat atctaaatac tcttaagaaa tgaccagtct gaggctgtaa tgtcgtccaa    1380
attcggaagt tgagaaaaca tttgtgaatc cccattacct tcctgatgtt gtggttgaat    1440
cttatctgaa tggaaatgat gtcgtggttc attagaaatg gcctctggct gtgttctgtt    1500
atcttgaaat agaggggggat tgttatctcc cagataaaaa cgccattctc tgcctgagga    1560
gcagtgatga gttcccctgt gcgtgaatcc atgattattg cagttgaggt ggaggtagta    1620
tgagcagcca cagtctaggt ctacacgctt acgccttatt ggtttcttct tggctatctt    1680
gtgttggacc ttgattgata cttgcgaaca gtggctcgta gagggtgacg aaggttgcat    1740
tcttgagagc ccaattttc aaggatatgt tttttcttc gtctagatat tccctatatg    1800
atgaggtagg tcctggattg cagaggaaga tagtgggaat tccccctta atttgaatgg    1860
gcttcccgta ctttgtgttg ctttgccagt ccctctgggc ccccatgaat tccttgaagt    1920
gctttaaata atgcgggtct acgtcatcaa tgacgttgta ccacgcatca ttactgtaca    1980
cctttgggct taggtctaga tgtccacata aataattatg tgggcctaga gacctggccc    2040
acattgtttt gcctgttctg ctatcaccct caatgacaat acttatgggt ctccatggcc    2100
gcgcagcgga atacacgacg ttctcggcga cccactcttc aagttcatct ggaacttgat    2160
taaaagaaga agaaagaaat ggagaaacat aaacttctaa aggaggacta aaaatcctat    2220
```

```
ctaaatttga acttaaatta tgaaattgta aaatatagtc ctttggggcc ttctctttta   2280
atatattgag ggcctcggat ttactgcctg aattgagtgc ttcggcatat gcgtcgttgg   2340
cagattgctg acctcctcta gctgatctgc catcgatttg gaaaactcca aaatcaatga   2400
agtctccgtc tttctccacg taggtcttga catctgttga gctcttagct gcctgaatgt   2460
tcggatggaa atgtgctgac ctgtttggtg ataccaggtc gaagaaccgt tggttcttac   2520
attggtattt gccttcgaat tggataagca catggagatg tggttcccca ttctcgtgga   2580
gttctctgca aactttgatg tattttttat ttgttggggt ttctaggttt tttaattggg   2640
aaagtgcttc ctctttagag agagaacaat tgggatatgt taggaaataa tttttggcat   2700
atattttaaa taaacgaggc at                                             2722

<210> SEQ ID NO 3
<211> LENGTH: 238
<212> TYPE: PRT
<213> ORGANISM: Artificial sequence
<220> FEATURE:
<223> OTHER INFORMATION: IL-60 coat protein
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 3

Met Ser Xaa Arg Pro Gly Asp Ile Ile Ile Ser Thr Pro Val Ser Lys
1               5                   10                  15

Val Arg Arg Arg Leu Asn Phe Xaa Gly Pro Tyr Arg Xaa Met Tyr Arg
            20                  25                  30

Lys Pro Arg Asn Thr Glu Cys Ile Glu Ala Leu Met Phe Pro Val Asp
        35                  40                  45

Val Lys Ala Pro Leu Lys Xaa Ser Xaa Met Ser Asn Gly Met Ile Leu
    50                  55                  60

Ser Xaa Leu Val Leu Phe Gly Cys Val Xaa Asp Val Thr Xaa Gly Ser
65                  70                  75                  80

Gly Ile Thr His Arg Val Gly Lys Arg Phe Cys Val Lys Ser Ile Tyr
                85                  90                  95

Phe Leu Gly Lys Val Trp Met Asp Glu Asn Ile Lys Lys Gln Asn His
            100                 105                 110
```

```
Thr Asn Gln Val Met Phe Phe Leu Val Arg Asp Arg Pro Tyr Gly
        115                 120                 125
Asn Ser Pro Met Asp Phe Gly Gln Val Phe Asn Met Phe Asp Asn Glu
    130                 135                 140
Pro Ser Thr Ala Thr Val Lys Asn Asp Leu Arg Asp Arg Phe Gln Val
145                 150                 155                 160
Met Arg Lys Phe His Ala Thr Val Ile Gly Gly Pro Ser Gly Met Lys
                165                 170                 175
Glu Gln Ala Leu Val Lys Arg Phe Phe Lys Ile Asn Ser His Val Thr
            180                 185                 190
Tyr Asn His Gln Glu Ala Ala Lys Tyr Glu Asn His Thr Glu Asn Ala
        195                 200                 205
Leu Leu Leu Tyr Met Ala Cys Thr His Ala Ser Asn Pro Val Tyr Ala
    210                 215                 220
Thr Met Lys Ile Arg Ile Tyr Phe Tyr Asp Ser Ile Ser Asn
225                 230                 235
```

<210> SEQ ID NO 4
<211> LENGTH: 2787
<212> TYPE: DNA
<213> ORGANISM: tomato yellow leaf curl virus

<400> SEQUENCE: 4

```
gttgaaatga atcggtgtcc ctcaaagctc tatggcaatc ggtgtatcgg tgtcttactt      60
atacttggac acctaatggc tatttggtaa tttcataaat gttcatttca attcaaaatt     120
caaaattcaa aaatcaaatc attaaagcgg ccatccgtat aatattaccg gatggccgcg     180
ccttttcctt ttatgtggtc cccacgaggg ttacacagat gttattgtca accaatcaaa     240
ttgcattctc aaacgttaga taagtgttca tttgtcttta tacttggt ccccaagttt      300
tttgtcttgc aatatgtggg acccacttct taatgaattt cctgaatctg ttcacggatt     360
tcgttgtatg ttagctatta aatatttgca gtccgttgag gaaacttacg agcccaatac     420
attgggccac gatttaatta gggatcttat atctgttgta agggcccgtg actatgtcga     480
agcgaccagg cgatataatc atttccacgc ccgtctcgaa ggttcgccga aggctgaact     540
tcgacagccc atacagcagc cgtgctgctg tccccattgt ccaaggcaca aacaagcgac     600
gatcatggac gtacaggccc atgtaccgaa agcccagaat atacagaatg tatcgaagcc     660
ctgatgttcc ccgtggatgt gaaggcccat gtaaagtcca gtcttatgag caacgggatg     720
atattaagca tactggtatt gttcgttgtg ttagtgatgt tactcgtgga tctggaatta     780
ctcacagagt gggtaagagg ttctgtgtta aatcgatata tttttaggt aaagtctgga     840
tggatgaaaa tatcaagaag cagaatcaca ctaatcaggt catgttcttc ttggtccgtg     900
atagaaggcc ctatggaaac agcccaatgg attttggaca ggttttaat atgttcgata    960
atgagcccag taccgcaacc gtgaagaatg atttgcgtga taggtttcaa gtgatgagga   1020
aatttcatgc tacagttatt ggtgggccct ctggaatgaa ggaacaggca ttagttaaga   1080
gatttttaa aattaacagt catgtaactt tatttatatt cattcaggag gcagcaaagt   1140
acgagaacca tactgaaaac gccttgttat tgtatatggc atgtacgcat gcctctaatc   1200
cagtgtatgc aactatgaaa atacgcatct attctatga ttcaatatca attaataaa    1260
atttatattt tatatcatga gtttctgtta catttattgt gttttcaagt acatcataca   1320
atacatgatc aactgctctg attacattgt taatggaaat tacaccaaga ctatctaaat   1380
acttaagaac ttcatatcta aatactctta agaaatgacc agtctgaggc tgtaatgtcg   1440
```

```
tccaaattcg gaagtcgaga aaacatttgt gaatccccat taccttcctg atgttgtggt    1500
tgaatcttat ctgaatggaa atgatgtcgt ggttcattag aaatggcctc tggctgtgtt    1560
ctgttatctt gaaatagagg ggattgttta tctcccagat aaaaacgcca ttctctgcct    1620
gaggagcagt gatgagttcc cctgtgcgtg aatccatgat tattgcagtt gaggtggagg    1680
tagtatgagc agccacagtc taggtctaca cgcttacgcc ttattggttt cttcttggct    1740
atcttgtgtt ggaccttgat tgatacttgc gaacagtggc tcgtagaggg tgacgaaggt    1800
tgcattcttg agagcccaat ttttcaagga tatgttttt tcttcgtcta gatattccct     1860
atatgaggag gtaggtcctg gattgcagag gaagatagtg ggaattcccc ctttaatttg    1920
aatgggcttc ccgtactttg tgttgctttg ccagtccctc tgggcccca tgaattcctt     1980 gaagtgcttt aaataatgcg ggtctacgtc atcaatgacg ttgtaccacg catcattact    2040
gtacaccttt gggcttaggt ctagatgtcc acataaataa ttatgtgggc ctagagacct    2100
ggcccacatt gttttgcctg ttctgctatc accctcaatg acaatactta tgggtctcca    2160
tggccgcgca gcggaataca cgacgttctc ggcgacccac tcttcaagtt catctggaac    2220
ttgattaaaa aagaagaaa gaaatggaga acataaact tctaaggag gactaaaaat       2280 cctatctaaa tttgaactta aattatgaaa ttgtaaaata tagtcctttg gggccttctc    2340
ttttaatata ttgagggcct cggatttact gcctgaattg agtgcttcgg catatgcgtc    2400
gttggcagat tgctgacctc ctctagctga tctgccatcg atttgggaaa ctccaaaatc    2460
aatgaagttt ccgtctttct ccacgtaggt cttgacatct gttgagctct tagctgcctg    2520
aatgttcgga tggaaatgtg ctgacctgtt tggggatacc aagtcgaaga accgttggtt    2580
cttacattgg tatttgcctt cgaattggat aagcacatgg agatgtggtt ccccattctc    2640
gtggagttct ttgcaaactt tgatgtattt tttatttgtt ggggtttcta gtttttttaa    2700
ttgggaaagt gcttcctctt tagagagaga acaattggga tatgttagga ataattttt    2760 ggcatatatt ttaaataaac gaggcat                                        2787
```

<210> SEQ ID NO 5
<211> LENGTH: 280
<212> TYPE: PRT
<213> ORGANISM: Tomato yellow leaf curl virus

<400> SEQUENCE: 5

```
Met Ser Lys Arg Pro Gly Asp Ile Ile Ile Ser Thr Pro Val Ser Lys
1               5                   10                  15

Val Arg Arg Arg Leu Asn Phe Asp Ser Pro Tyr Ser Ser Arg Ala Ala
            20                  25                  30

Val Pro Ile Val Gln Gly Thr Asn Lys Arg Arg Ser Trp Thr Tyr Arg
        35                  40                  45

Pro Met Tyr Arg Lys Pro Arg Ile Tyr Arg Met Tyr Arg Ser Pro Asp
    50                  55                  60

Val Pro Arg Gly Cys Glu Gly Pro Cys Lys Val Gln Ser Tyr Glu Gln
65                  70                  75                  80

Arg Asp Asp Ile Lys His Thr Gly Ile Val Arg Cys Val Ser Asp Val
                85                  90                  95

Thr Arg Gly Ser Gly Ile Thr His Arg Val Gly Lys Arg Phe Cys Val
            100                 105                 110

Lys Ser Ile Tyr Phe Leu Gly Lys Val Trp Met Asp Glu Asn Ile Lys
        115                 120                 125

Lys Gln Asn His Thr Asn Gln Val Met Phe Phe Leu Val Arg Asp Arg
```

```
                130                 135                 140
Arg Pro Tyr Gly Asn Ser Pro Met Asp Phe Gly Gln Val Phe Asn Met
145                 150                 155                 160

Phe Asp Asn Glu Pro Ser Thr Ala Thr Val Lys Asn Asp Leu Arg Asp
                165                 170                 175

Arg Phe Gln Val Met Arg Lys Phe His Ala Thr Val Ile Gly Gly Pro
                180                 185                 190

Ser Gly Met Lys Glu Gln Ala Leu Val Lys Arg Phe Phe Lys Ile Asn
                195                 200                 205

Ser His Val Thr Leu Phe Ile Phe Ile Gln Glu Ala Ala Lys Tyr Glu
                210                 215                 220

Asn His Thr Glu Asn Ala Leu Leu Leu Tyr Met Ala Cys Thr His Ala
225                 230                 235                 240

Ser Asn Pro Val Tyr Ala Thr Met Lys Ile Arg Ile Tyr Phe Tyr Asp
                245                 250                 255

Ser Ile Ser Asn Ser Asn Pro Val Tyr Ala Thr Met Lys Ile Arg Ile
                260                 265                 270

Tyr Phe Tyr Asp Ser Ile Ser Asn
                275                 280

<210> SEQ ID NO 6
<211> LENGTH: 116
<212> TYPE: PRT
<213> ORGANISM: Tomato yellow leaf curl virus

<400> SEQUENCE: 6

Met Trp Asp Pro Leu Leu Asn Glu Phe Pro Glu Ser Val His Gly Phe
1               5                   10                  15

Arg Cys Met Leu Ala Ile Lys Tyr Leu Gln Ser Val Glu Glu Thr Tyr
                20                  25                  30

Glu Pro Asn Thr Leu Gly His Asp Leu Ile Arg Asp Leu Ile Ser Val
                35                  40                  45

Val Arg Ala Arg Asp Tyr Val Glu Ala Thr Arg Arg Tyr Asn His Phe
            50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
                85                  90                  95

Ile Met Asp Val Gln Ala His Val Pro Lys Ala Gln Asn Ile Gln Asn
                100                 105                 110

Val Ser Lys Pro
        115

<210> SEQ ID NO 7
<211> LENGTH: 357
<212> TYPE: PRT
<213> ORGANISM: Tomato yellow leaf curl virus
<220> FEATURE:
<221> NAME/KEY: misc_feature
<223> OTHER INFORMATION: Rep protein of the Tomato yellow leaf curl
      virus

<400> SEQUENCE: 7

Met Pro Arg Leu Phe Lys Ile Tyr Ala Lys Asn Tyr Phe Leu Thr Tyr
1               5                   10                  15

Pro Asn Cys Ser Leu Ser Lys Glu Glu Ala Leu Ser Gln Leu Lys Lys
                20                  25                  30

Leu Glu Thr Pro Thr Asn Lys Lys Tyr Ile Lys Val Cys Lys Glu Leu
```

```
                35                  40                  45
His Glu Asn Gly Glu Pro His Leu His Val Leu Ile Gln Phe Glu Gly
 50                  55                  60

Lys Tyr Gln Cys Lys Asn Gln Arg Phe Phe Asp Leu Val Ser Pro Asn
 65                  70                  75                  80

Arg Ser Ala His Phe His Pro Asn Ile Gln Ala Ala Lys Ser Ser Thr
                 85                  90                  95

Asp Val Lys Thr Tyr Val Glu Lys Asp Gly Asn Phe Ile Asp Phe Gly
            100                 105                 110

Val Ser Gln Ile Asp Gly Arg Ser Ala Arg Gly Gly Gln Gln Ser Ala
        115                 120                 125

Asn Asp Ala Tyr Ala Glu Ala Leu Asn Ser Gly Ser Lys Ser Glu Ala
130                 135                 140

Leu Asn Ile Leu Lys Glu Lys Ala Pro Lys Asp Tyr Ile Leu Gln Phe
145                 150                 155                 160

His Asn Leu Ser Ser Asn Leu Asp Arg Ile Phe Ser Pro Pro Leu Glu
                165                 170                 175

Val Tyr Val Ser Pro Phe Leu Ser Ser Ser Phe Asn Gln Val Pro Asp
            180                 185                 190

Glu Leu Glu Glu Trp Val Ala Glu Asn Val Val Tyr Ser Ala Ala Arg
        195                 200                 205

Pro Trp Arg Pro Ile Ser Ile Val Ile Glu Gly Asp Ser Arg Thr Gly
210                 215                 220

Lys Thr Met Trp Ala Arg Ser Leu Gly Pro His Asn Tyr Leu Cys Gly
225                 230                 235                 240

His Leu Asp Leu Ser Pro Lys Val Tyr Ser Asn Asp Ala Trp Tyr Asn
                245                 250                 255

Val Ile Asp Asp Val Asp Pro His Tyr Leu Lys His Phe Lys Glu Phe
            260                 265                 270

Met Gly Ala Gln Arg Asp Trp Gln Ser Asn Thr Lys Tyr Gly Lys Pro
        275                 280                 285

Ile Gln Ile Lys Gly Gly Ile Pro Thr Ile Phe Leu Cys Asn Pro Gly
290                 295                 300

Pro Thr Ser Ser Tyr Arg Glu Tyr Leu Asp Glu Glu Lys Asn Ile Ser
305                 310                 315                 320

Leu Lys Asn Trp Ala Leu Lys Asn Ala Thr Phe Val Thr Leu Tyr Glu
                325                 330                 335

Pro Leu Phe Ala Ser Ile Asn Gln Gly Pro Thr Gln Asp Ser Gln Glu
            340                 345                 350

Glu Thr Asn Lys Ala
        355

<210> SEQ ID NO 8
<211> LENGTH: 98
<212> TYPE: PRT
<213> ORGANISM: Tomato yellow leaf curl virus
<220> FEATURE:
<221> NAME/KEY: misc_feature
<223> OTHER INFORMATION: C4 polypeptide

<400> SEQUENCE: 8

Arg Met Gly Asn His Ile Ser Met Cys Leu Ser Asn Ser Lys Ala Asn
 1               5                  10                  15

Thr Asn Val Arg Thr Asn Gly Ser Ser Thr Trp Tyr Pro Gln Thr Gly
                20                  25                  30

Gln His Ile Ser Ile Arg Thr Phe Arg Gln Leu Arg Ala Gln Gln Met
```

```
              35                  40                  45
Ser Arg Pro Thr Trp Arg Lys Thr Glu Thr Ser Leu Ile Leu Glu Phe
        50                  55                  60

Pro Lys Ser Met Ala Asp Gln Leu Glu Glu Val Ser Asn Leu Pro Thr
65                  70                  75                  80

Thr His Met Pro Lys His Ser Ile Gln Ala Val Asn Pro Arg Pro Ser
                85                  90                  95

Ile Tyr

<210> SEQ ID NO 9
<211> LENGTH: 9
<212> TYPE: DNA
<213> ORGANISM: Artificial sequence
<220> FEATURE:
<223> OTHER INFORMATION: IR universal motif

<400> SEQUENCE: 9 taatattac                                                                 9

<210> SEQ ID NO 10
<211> LENGTH: 1486
<212> TYPE: DNA
<213> ORGANISM: Artificial sequence
<220> FEATURE:
<223> OTHER INFORMATION: C1(truncated)- C4 (truncated)-IR-V2-V1

<400> SEQUENCE: 10
gttgagctct tagctgcctg aatgttcgga tggaaatgtg ctgacctgtt tggtgatacc         60
aggtcgaaga accgttggtt cttacattgg tatttgcctt cgaattggat aagcacatgg        120
agatgtggtt ccccattctc gtggagttct ctgcaaactt tgatgtattt tttatttgtt        180
ggggtttcta ggtttttaa ttgggaaagt gcttcctctt tagagagaga acaattggga         240
tatgttagga ataatttttt ggcatatatt ttaaataaac gaggcatgtt gaatgaatc         300 ggtgtctctc aaagctctat ggcaatcggt gtatcggtgt cttacttata cctggacacc        360
taatggctat ttggtaattt cataaatgtt cattgcaatt caaaattcaa aattcaaaaa        420
tcaaatcttt aaagcggcca tccgtataat attaccggat ggccgcgcct tttgttttta        480
tgtggtcccc acgagggtta cacagacgtc actgtcaacc aatcaaattg cattctcaaa        540
cgttagataa gtgttcattt gtctttatat acttggtccc aagttttttt gtcttgcaat        600
atgtgggacc cacttcttaa tgaatttcct gaatctgttc acggatttcg ttgtatgtta        660
gctattaaat atttgcagtc cgttgaggaa acttacgagc ccaatacatt gggccacgat        720
ttaattaggg atcttatatc tgttgtaagg gcccgtgact atgtcgaagc gaccaggcga        780
tataatcatt tccacgcccg tctcgaaggt tcgccgaagg ctgaacttcg acagcccata        840
caggcccatg taccgaaagc ccagaatata cagaatgtat cgaagccctg atgttccccg        900
tggatgtgaa ggcccatgta aagtccagtc ttatgagcaa cgggatgata ttaagcatac        960
tggtattgtt cgttgtgtta gtgatgttac tcgtggatct ggaattactc acagagtggg       1020
taagaggttc tgtgttaaat cgatatattt tttaggtaaa gtctggatgg atgaaaatat       1080
caagaagcag aatcacacta atcaggtcat gttcttcttg gtccgtgata gaaggcccta       1140
tggaaacagc ccaatggatt ttggacaggt ttttaatatg ttcgataatg agcccagtac       1200
cgcaaccgtg aagaatgatt tgcgtgatag gtttcaagtg atgaggaaat tcatgctac       1260 agttattggt gggcccctg gaatgaagga acaggcatta gttaagagat tttttaaaat       1320
taacagtcat gtaacttata atcatcagga ggcagcaaag tacgagaacc atactgaaaa       1380
```

| | |
|---|---|
| cgccttgtta ttgtatatgg catgtacgca tgcctctaat ccagtgtatg caactatgaa | 1440 |
| aatacgcatc tatttctatg attcaatatc aaattaatgg atccac | 1486 |

<210> SEQ ID NO 11
<211> LENGTH: 1190
<212> TYPE: DNA
<213> ORGANISM: Artificial sequence
<220> FEATURE:
<223> OTHER INFORMATION: IR-V2-V1

<400> SEQUENCE: 11

| | |
|---|---|
| gttgaaatga atcggtgtct ctcaaagctc tatggcaatc ggtgtatcgg tgtcttactt | 60 |
| atacctggac acctaatggc tatttggtaa tttcataaat gttcattgca attcaaaatt | 120 |
| caaaattcaa aaatcaaatc tttaaagcgg ccatccgtat aatattaccg gatggccgcg | 180 |
| ccttttgttt ttatgtggtc cccacgaggg ttacacagac gtcactgtca accaatcaaa | 240 |
| ttgcattctc aaacgttaga taagtgttca tttgtcttta tatacttggt ccccaagttt | 300 |
| tttgtcttgc aatatgtggg acccacttct taatgaattt cctgaatctg ttcacggatt | 360 |
| tcgttgtatg ttagctatta aatatttgca gtccgttgag gaaacttacg agcccaatac | 420 |
| attgggccac gatttaatta gggatcttat atctgttgta agggcccgtg actatgtcga | 480 |
| agcgaccagg cgatataatc atttccacgc ccgtctcgaa ggttcgccga aggctgaact | 540 |
| tcgacagccc atacaggccc atgtaccgaa agcccagaat atacagaatg tatcgaagcc | 600 |
| ctgatgttcc ccgtggatgt gaaggcccat gtaaagtcca gtcttatgag caacgggatg | 660 |
| atattaagca tactggtatt gttcgttgtg ttagtgatgt tactcgtgga tctggaatta | 720 |
| ctcacagagt gggtaagagg ttctgtgtta aatcgatata tttttttaggt aaagtctgga | 780 |
| tggatgaaaa tatcaagaag cagaatcaca ctaatcaggt catgttcttc ttggtccgtg | 840 |
| atagaaggcc ctatggaaac agcccaatgg attttggaca ggttttttaat atgttcgata | 900 |
| atgagcccag taccgcaacc gtgaagaatg atttgcgtga taggtttcaa gtgatgagga | 960 |
| aatttcatgc tacagttatt ggtgggccct ctggaatgaa ggaacaggca ttagttaaga | 1020 |
| gatttttttaa aattaacagt catgtaactt ataatcatca ggaggcagca aagtacgaga | 1080 |
| accatactga aaacgccttg ttattgtata tggcatgtac gcatgcctct aatccagtgt | 1140 |
| atgcaactat gaaaatacgc atctatttct atgattcaat atcaaattaa | 1190 |

<210> SEQ ID NO 12
<211> LENGTH: 4264
<212> TYPE: DNA
<213> ORGANISM: Artificial sequence
<220> FEATURE:
<223> OTHER INFORMATION: IR-pD
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t

<400> SEQUENCE: 12

| | |
|---|---|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg ccaagctcta | 240 |

```
atacgactca ctatagggaa agctcggtac cacgcatgct gcagacgcgt tacgtatcgg    300
atccagaatt cgtgatatct gaattcatac ctggacacct aatggctatt tggtaatttc    360
ataaatgttc attgcaattc aaaattcaaa attcaaaaat caaatcttta aagcggccat    420
ccgtataata ttaccggatg gccgcgcctt ttgttttttat gtggtcccca cgagggttac    480
acagacgtca ctgtcaacca atcaaattgc attctcaaac gttagataag tgttcatttg    540
tctttatata cttggtcccc aagttttttg tcttgcaata tgtgggaccc acttcttaat    600
gaatttcctg aatctgttca cggatttcgt tgtatgttag ctattaaata tttgcagtcc    660
gttgaggaaa cttacgagcc caatacattg gccacgatt taattangga tcttatatct    720
gttgtaaggg cccngtgacg tcgacaagct tctcgagcct aggctagctc tagaccacac    780 gtgtggggc ccgagctcgc ggccgctgta ttctatagtg tcacctaaat ggccgcacaa    840
ttcactggcc gtcgttttac aacgtcgtga ctgggaaaac cctggcgtta cccaacttaa    900
tcgccttgca gcacatcccc ctttcgccag ctggcgtaat agcgaagagg cccgcaccga    960
tcgcccttcc caacagttgc gcagcctgaa tggcgaatgg aaattgtaag cgttaatatt    1020
ttgttaaaat tcgcgttaaa ttttttgttaa atcagctcat tttttaacca ataggccgaa    1080
atcggcaaaa tcccttataa atcaaaagaa tagaccgaga tagggttgag tgttgttcca    1140
gtttggaaca agagtccact attaaagaac gtggactcca acgtcaaagg gcgaaaaacc    1200
gtctatcagg gcgatggccc actacgtgaa ccatcaccct aatcaagttt ttggggtcg     1260 aggtgccgta aagcactaaa tcggaaccct aaagggagcc cccgatttag agcttgacgg    1320
ggaaagccgg cgaacgtggc gagaaaggaa gggaagaaag cgaaaggagc gggcgctagg    1380
gcgctggcaa gtgtagcggt cacgctgcgc gtaaccacca cacccgccgc gcttaatgcg    1440
ccgctacagg gcgcgtcagg tggcactttt cggggaaatg tgcgcggaac ccctatttgt    1500
ttatttttct aaatacattc aaatatgtat ccgctcatga caataaccc tgataaatg     1560 cttcaataat attgaaaaag gaagagtatg agtattcaac atttccgtgt cgcccttatt    1620 ccctttttg cggcattttg ccttcctgtt tttgctcacc cagaaacgct ggtgaaagta     1680
aaagatgctg aagatcagtt gggtgcacga gtgggttaca tcgaactgga tctcaacagc    1740
ggtaagatcc ttgagagttt tcgccccgaa gaacgttttc caatgatgag cacttttaaa    1800
gttctgctat gtggcgcggt attatcccgt attgacgccg ggcaagagca actcggtcgc    1860
cgcatacact attctcagaa tgacttggtt gagtactcac cagtcacaga aaagcatctt    1920
acggatggca tgacagtaag agaattatgc agtgctgcca taaccatgag tgataacact    1980
gcggccaact tacttctgac aacgatcgga ggaccgaagg agctaaccgc ttttttgcac    2040
aacatggggg atcatgtaac tcgccttgat cgttgggaac cggagctgaa tgaagccata    2100
ccaaacgacg agcgtgacac cacgatgcct gtagcaatgg caacaacgtt gcgcaaacta    2160
ttaactggcg aactacttac tctagcttcc cggcaacaat aatagactg gatggaggcg    2220 gataaagttg caggaccact tctgcgctcg gcccttccgg ctggctggtt tattgctgat    2280
aaatctggag ccggtgagcg tgggtctcgc ggtatcattg cagcactggg gccagatggt    2340
aagccctccc gtatcgtagt tatctacacg acggggagtc aggcaactat ggatgaacga    2400
aatagacaga tcgctgagat aggtgcctca ctgattaagc attggtaact gtcagaccaa    2460
gtttactcat atatacttta gattgattta aaacttcatt tttaatttaa aaggatctag    2520
gtgaagatcc tttttgataa tctcatgaac aataaaactg tctgcttaca taaacagtaa    2580 tacaagggt gttatgagcc atattcaacg ggaaacgtct tgctctaggc cgcgattaaa    2640
```

| | |
|---|---|
| ttccaacatg gatgctgatt tatatgggta taaatgggct cgcgataatg tcgggcaatc | 2700 |
| aggtgcgaca atctatcgat tgtatgggaa gcccgatgcg ccagagttgt ttctgaaaca | 2760 |
| tggcaaaggt agcgttgcca atgatgttac agatgagatg gtcagactaa actggctgac | 2820 |
| ggaatttatg cctcttccga ccatcaagca tttatccgt actcctgatg atgcatggtt | 2880 |
| actcaccact gcgatccccg ggaaaacagc attccaggta ttagaagaat atcctgattc | 2940 |
| aggtgaaaat attgttgatg cgctggcagt gttcctgcgc cggttgcatt cgattcctgt | 3000 |
| ttgtaattgt ccttttaaca gcgatcgcgt atttcgtctc gctcaggcgc aatcacgaat | 3060 |
| gaataacggt ttggttgatg cgagtgattt tgatgacgag cgtaatggct ggcctgttga | 3120 |
| acaagtctgg aaagaaatgc ataaactttt gccattctca ccggattcag tcgtcactca | 3180 |
| tggtgatttc tcacttgata accttatttt tgacgagggg aaattaatag gttgtattga | 3240 |
| tgttggacga gtcggaatcg cagaccgata ccaggatctt gccatcctat ggaactgcct | 3300 |
| cggtgagttt tctccttcat tacagaaacg gcttttttcaa aaatatggta ttgataatcc | 3360 |
| tgatatgaat aaattgcagt ttcatttgat gctcgatgag tttttctaag aattaattca | 3420 |
| tgaccaaaat cccttaacgt gagttttcgt tccactgagc gtcagacccc gtagaaaaga | 3480 |
| tcaaaggatc ttcttgagat cctttttttc tgcgcgtaat ctgctgcttg caaacaaaaa | 3540 |
| aaccaccgct accagcggtg gtttgtttgc cggatcaaga gctaccaact cttttttccga | 3600 |
| aggtaactgg cttcagcaga gcgcagatac caaatactgt ccttctagtg tagccgtagt | 3660 |
| taggccacca cttcaagaac tctgtagcac cgcctacata cctcgctctg ctaatcctgt | 3720 |
| taccagtggc tgctgccagt ggcgataagt cgtgtcttac cgggttggac tcaagacgat | 3780 |
| agttaccgga taaggcgcag cggtcgggct gaacggggg ttcgtgcaca cagcccagct | 3840 |
| tggagcgaac gacctacacc gaactgagat acctacagcg tgagctatga gaaagcgcca | 3900 |
| cgcttcccga agggagaaag gcggacaggt atccggtaag cggcagggtc ggaacaggag | 3960 |
| agcgcacgag ggagcttcca gggggaaacg cctggtatct ttatagtcct gtcgggtttc | 4020 |
| gccacctctg acttgagcgt cgatttttgt gatgctcgtc aggggggcgg agcctatgga | 4080 |
| aaaacgccag caacgcggcc ttttacggt tcctggcctt ttgctggcct tttgctcaca | 4140 |
| tgttctttcc tgcgttatcc cctgattctg tggataaccg tattaccgcc tttgagtgag | 4200 |
| ctgataccgc tcgccgcagc cgaacgaccg agcgcagcga gtcagtgagc gaggaagcgg | 4260 |
| aaga | 4264 |

<210> SEQ ID NO 13
<211> LENGTH: 6035
<212> TYPE: DNA
<213> ORGANISM: Artificial sequence
<220> FEATURE:
<223> OTHER INFORMATION: IR-GUS-pD
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t

<400> SEQUENCE: 13

| | |
|---|---|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |

```
tgtgagcgga taacaatttc acacaggaaa cagctatgac catgattacg ccaagctcta    240
atacgactca ctatagggaa agctcggtac cacgcatgct gcagacgcgt tacgtatcgg    300
atccagaatt cgtgatatct gaattcatac ctggacacct aatggctatt tggtaatttc    360
ataaatgttc attgcaattc aaaattcaaa attcaaaaat caaatcttta aagcggccat    420
ccgtataata ttaccggatg gccgcgcctt ttgtttttat gtggtcccca cgagggttac    480
acagacgtca ctgtcaacca atcaaattgc attctcaaac gttagataag tgttcatttg    540
tctttatata cttggtcccc aagttttttg tcttgcaata tgtgggaccc acttcttaat    600
gaatttcctg aatctgttca cggatttcgt tgtatgttag ctattaaata tttgcagtcc    660
gttgaggaaa cttacgagcc caatacattg ggccacgatt taattangga tcttatatct    720
gttgtaaggg cccngtgacg aattcgtcga catgttacgt cctgtagaaa ccccaacccg    780
tgaaatcaaa aaactcgacg gcctgtgggc attcagtctg gatcgcgaaa actgtggaat    840
tgatcagcgt tggtgggaaa gcgcgttaca agaaagccgg gcaattgctg tgccaggcag    900
ttttaacgat cagttcgccg atgcagatat tcgtaattat gcgggcaacg tctggtatca    960
gcgcgaagtc tttataccga aaggttgggc aggccagcgt atcgtgctgc gtttcgatgc    1020
ggtcactcat tacggcaaag tgtgggtcaa taatcaggaa gtgatggagc atcagggcgg    1080
ctatacgcca tttgaagccg atgtcacgcc gtatgttatt gccgggaaaa gtgtacgtat    1140
caccgtttgt gtgaacaacg aactgaactg gcagactatc ccgccgggaa tggtgattac    1200
cgacgaaaac ggcaagaaaa agcagtctta cttccatgat ttctttaact atgccgggat    1260
ccatcgcagc gtaatgctct acaccacgcc gaacacctgg gtggacgata tcaccgtggt    1320
gacgcatgtc gcgcaagact gtaaccacgc gtctgttgac tggcaggtgg tggccaatgg    1380
tgatgtcagc gttgaactgc gtgatgcgga tcaacaggtg gttgcaactg acaaggcac     1440 tagcgggact ttgcaagtgg tgaatccgca cctctggcaa ccgggtgaag ttatctcta    1500 tgaactgtgc gtcacagcca aaagccagac agagtgtgat atctacccgc ttcgcgtcgg    1560
catccggtca gtggcagtga agggcgaaca gttcctgatt aaccacaaac cgttctactt    1620 tactggctt t ggtcgtcatg aagatgcgga cttacgtggc aaaggattcg ataacgtgct    1680
gatggtgcac gaccacgcat taatggactg gattggggcc aactcctacc gtacctcgca    1740
ttacccttac gctgaagaga tgctcgactg gcagatgaa catggcatcg tggtgattga    1800
tgaaactgct gctgtcggct ttaacctctc tttaggcatt ggtttcgaag cgggcaacaa    1860
gccgaaagaa ctgtacagcg aagaggcagt caacggggaa actcagcaag cgcacttaca    1920
ggcgattaaa gagctgatag cgcgtgacaa aaaccaccca agcgtggtga tgtggagtat    1980
tgccaacgaa ccggataccc gtccgcaagt gcacgggaat atttcgccac tggcggaagc    2040
aacgcgtaaa ctcgacccga cgcgtccgat cacctgcgtc aatgtaatgt tctgcgacgc    2100
tcacaccgat accatcagcg atctctttga tgtgctgtgc ctgaaccgtt attacggatg    2160
gtatgtccaa agcggcgatt tggaaacggc agagaaggta ctggaaaaag aacttctggc    2220
ctggcaggag aaactgcatc agccgattat catcaccgaa tacggcgtgg atacgttagc    2280
cgggctgcac tcaatgtaca ccgacatgtg gagtgaagag tatcagtgtg catggctgga    2340
tatgtatcac cgcgtctttg atcgcgtcag cgccgtcgtc ggtgaacagg tatggaattt    2400
cgccgatttt gcgacctcgc aaggcatatt gcgcgttggc ggtaacaaga agggatctt    2460 cactcgcgac cgcaaaccga gtcggcggc ttttctgctg caaaaacgct ggactggcat    2520
gaacttcggt gaaaaaccgc agcagggagg caaacagtcg acatcagctc gcggccgctg    2580
```

```
tattctatag tgtcacctaa atggccgcac aattcactgg ccgtcgtttt acaacgtcgt    2640
gactgggaaa accctggcgt tacccaactt aatcgccttg cagcacatcc cccttccgcc    2700
agctggcgta atagcgaaga ggcccgcacc gatcgccctt cccaacagtt gcgcagcctg    2760
aatggcgaat ggaaattgta agcgttaata ttttgttaaa attcgcgtta aattttgtt     2820 aaatcagctc attttttaac caataggccg aaatcggcaa aatcccttat aaatcaaaag    2880
aatagaccga gatagggttg agtgttgttc cagtttggaa caagagtcca ctattaaaga    2940
acgtggactc caacgtcaaa gggcgaaaaa ccgtctatca gggcgatggc ccactacgtg    3000
aaccatcacc ctaatcaagt tttttggggt cgaggtgccg taaagcacta aatcggaacc    3060
ctaaagggag cccccgattt agagcttgac ggggaaagcc ggcgaacgtg gcgagaaagg    3120
aagggaagaa agcgaaagga gcgggcgcta gggcgctggc aagtgtagcg gtcacgctgc    3180
gcgtaaccac cacacccgcc gcgcttaatg cgccgctaca gggcgcgtca ggtggcactt    3240
ttcggggaaa tgtgcgcgga acccctattt gtttattttt ctaaatacat tcaaatatgt    3300
atccgctcat gagacaataa ccctgataaa tgcttcaata atattgaaaa aggaagagta    3360
tgagtattca acatttccgt gtcgccctta ttcccttttt tgcggcattt tgccttcctg    3420 ttttgctca cccagaaacg ctggtgaaag taaagatgc tgaagatcag ttgggtgcac     3480
gagtgggtta catcgaactg gatctcaaca gcggtaagat ccttgagagt tttcgccccg    3540
aagaacgttt tccaatgatg agcactttta agttctgct atgtggcgcg gtattatccc    3600
gtattgacgc cgggcaagag caactcggtc gccgcataca ctattctcag aatgacttgg    3660
ttgagtactc accagtcaca gaaaagcatc ttacggatgg catgacagta agagaattat    3720
gcagtgctgc cataaccatg agtgataaca ctgcggccaa cttacttctg acaacgatcg    3780
gaggaccgaa ggagctaacc gcttttttgc acaacatggg ggatcatgta actcgccttg    3840
atcgttggga accggagctg aatgaagcca taccaaacga cgagcgtgac accacgatgc    3900
ctgtagcaat ggcaacaacg ttgcgcaaac tattaactgg cgaactactt actctagctt    3960
cccggcaaca attaatagac tggatggagg cggataaagt tgcaggacca cttctgcgct    4020
cggcccttcc ggctggctgg tttattgctg ataaatctgg agccggtgag cgtgggtctc    4080
gcggtatcat tgcagcactg gggccagatg gtaagccctc ccgtatcgta gttatctaca    4140
cgacggggag tcaggcaact atggatgaac gaaatagaca gatcgctgag ataggtgcct    4200
cactgattaa gcattggtaa ctgtcagacc aagtttactc atatatactt tagattgatt    4260
taaaacttca ttttaattt aaaaggatct aggtgaagat cctttttgat aatctcatga    4320
acaataaaac tgtctgctta cataaacagt aatacaaggg gtgttatgag ccatattcaa    4380
cgggaaacgt cttgctctag gccgcgatta aattccaaca tggatgctga tttatatggg    4440
tataaatggg ctcgcgataa tgtcgggcaa tcaggtgcga caatctatcg attgtatggg    4500
aagcccgatg cgccagagtt gtttctgaaa catggcaaag gtagcgttgc caatgatgtt    4560
acagatgaga tggtcagact aaactggctg acggaattta tgcctcttcc gaccatcaag    4620
cattttatcc gtactcctga tgatgcatgg ttactcacca ctgcgatccc cgggaaaaca    4680
gcattccagg tattagaaga atatcctgat tcaggtgaaa atattgttga tgcgctggca    4740
gtgttcctgc gccggttgca ttcgattcct gtttgtaatt gtccttttaa cagcgatcgc    4800
gtatttcgtc tcgctcaggc gcaatcacga atgaataacg gtttggttga tgcgagtgat    4860
tttgatgacg agcgtaatgg ctggcctgtt gaacaagtct ggaaagaaat gcataaactt    4920
ttgccattct caccggattc agtcgtcact catggtgatt tctcacttga taaccttatt    4980
```

-continued

```
tttgacgagg ggaaattaat aggttgtatt gatgttggac gagtcggaat cgcagaccga      5040
taccaggatc ttgccatcct atggaactgc ctcggtgagt tttctccttc attacagaaa      5100 cggcttttc aaaaatatgg tattgataat cctgatatga ataaattgca gtttcatttg       5160
atgctcgatg agttttcta agaattaatt catgaccaaa atcccttaac gtgagttttc       5220
gttccactga gcgtcagacc ccgtagaaaa gatcaaagga tcttcttgag atccttttt      5280 tctgcgcgta atctgctgct tgcaaacaaa aaaaccaccg ctaccagcgg tggtttgttt      5340
gccggatcaa gagctaccaa ctcttttcc gaaggtaact ggcttcagca gagcgcagat       5400
accaaatact gtccttctag tgtagccgta gttaggccac cacttcaaga actctgtagc      5460
accgcctaca tacctcgctc tgctaatcct gttaccagtg gctgctgcca gtggcgataa      5520
gtcgtgtctt accgggttgg actcaagacg atagttaccg gataaggcgc agcggtcggg      5580
ctgaacgggg ggttcgtgca cacagcccag cttggagcga acgacctaca ccgaactgag      5640
atacctacag cgtgagctat gagaaagcgc cacgcttccc gaagggagaa aggcggacag      5700
gtatccggta agcggcaggg tcggaacagg agagcgcacg agggagcttc caggggaaa       5760 cgcctggtat ctttatagtc ctgtcgggtt tcgccacctc tgacttgagc gtcgattttt      5820
gtgatgctcg tcagggggc ggagcctatg gaaaaacgcc agcaacgcgg cctttttacg       5880
gttcctggcc ttttgctggc cttttgctca catgttcttt cctgcgttat ccctgattc       5940 tgtggataac cgtattaccg cctttgagtg agctgatacc gctcgccgca gccgaacgac      6000
cgagcgcagc gagtcagtga gcgaggaagc ggaag                                 6035
```

<210> SEQ ID NO 14
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 14

```
acaggcccat agaccgaaag ccca                                             24
```

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' phosphorylated

<400> SEQUENCE: 15

```
tgggctgtcg aagttcagcc t                                                21
```

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16

```
attgggctgt ttccataggg c                                                21
```

<210> SEQ ID NO 17
<211> LENGTH: 19
<212> TYPE: DNA

```
<213> ORGANISM: Artificial sequence
<220> FEATURE:
<223> OTHER INFORMATION: Single strand DNA oligonucleotide

<400> SEQUENCE: 17
gaaggctgaa cttcgacag                                              19

<210> SEQ ID NO 18
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 18
tgtgtggaca ggtaatgg                                               18

<210> SEQ ID NO 19
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 19
ggccgaattc agtaaaggag aag                                         23

<210> SEQ ID NO 20
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 20
ggctgaactt cgacagccca tacagcagcc gtgctgctg                        39

<210> SEQ ID NO 21
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 21
gcggtactgg gctcattata tcgaacatat t                                31

<210> SEQ ID NO 22
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 22
ggcttcgata cattctgtat ttctg                                       25

<210> SEQ ID NO 23
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 23
ctgatgttcc ccgtggatgt gaaggcccat                                  30
```

<210> SEQ ID NO 24
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 24
ccacgagtaa catcactaac aaccaacaat ac                         32

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
attgatcagc gttggtggga                                       20

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
tgcggtcgcg agtgaagatc                                       20

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
gcgaacgaac acgatagcaa                                       20

<210> SEQ ID NO 28
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 28
cgtcaatgag ggcgtgaat                                        19

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
atacttggac acctaatggc                                       20

<210> SEQ ID NO 30
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 30
agtcacgggc ccttacaa                                                      18

<210> SEQ ID NO 31
<211> LENGTH: 1809
<212> TYPE: DNA
<213> ORGANISM: Artificial sequence
<220> FEATURE:
<223> OTHER INFORMATION: GusA coding sequence

<400> SEQUENCE: 31

```
atgttacgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat ttgaagccga tgtcacgccg     360
tatgttattg ccgggaaaag tgtacgtatc accgtttgtg tgaacaacga actgaactgg     420
cagactatcc cgccgggaat ggtgattacc gacgaaaacg gcaagaaaaa gcagtcttac     480
ttccatgatt tctttaacta tgccgggatc atcgcagcg taatgctcta caccacgccg     540
aacacctggg tggacgatat caccgtggtg acgcatgtcg cgcaagactg taaccacgcg     600
tctgttgact ggcaggtggt ggccaatggt gatgtcagcg ttgaactgcg tgatgcggat     660
caacaggtgg ttgcaactgg acaaggcact agcgggactt gcaagtggt gaatccgcac     720
ctctggcaac cgggtgaagg ttatctctat gaactgtgcg tcacagccaa agccagaca     780
gagtgtgata tctacccgct tcgcgtcggc atccggtcag tggcagtgaa gggcgaacag     840
ttcctgatta ccacaaaacc gttctacttt actggctttg gtcgtcatga agatgcggac     900
ttacgtggca aaggattcga taacgtgctg atggtgcacg accacgcatt aatggactgg     960
attgggccaa actcctaccg tacctcgcat taccttacg ctgaagagat gctcgactgg    1020
gcagatgaac atggcatcgt ggtgattgat gaaactgctg ctgtcggctt taacctctct    1080
ttaggcattg gtttcgaagc gggcaacaag ccgaaagaac tgtacagcga agaggcagtc    1140
aacgggaaa ctcagcaagc gcacttacag gcgattaaag agctgatagc gcgtgacaaa    1200
aaccacccaa gcgtggtgat gtggagtatt gccaacgaac cggatacccg tccgcaagtg    1260
cacgggaata tttcgccact ggcggaagca acgcgtaaac tcgacccgac gcgtccgatc    1320
acctgcgtca atgtaatgtt ctgcgacgct cacaccgata ccatcagcga tctctttgat    1380
gtgctgtgcc tgaaccgtta ttacggatgg tatgtccaaa gcggcgattt ggaaacggca    1440
gagaaggtac tggaaaaaga acttctggcc tggcaggaga aactgcatca gccgattatc    1500
atcaccgaat acggcgtgga tacgttagcc gggctgcact caatgtacac cgacatgtgg    1560
agtgaagagt atcagtgtgc atggctggat atgtatcacc gcgtctttga tcgcgtcagc    1620
gccgtcgtcg gtgaacaggt atggaatttc gccgattttg cgacctcgca aggcatattg    1680
cgcgttggcg gtaacaagaa agggatcttc actcgcgacc gcaaaccgaa gtcggcggct    1740
tttctgctgc aaaaacgctg gactggcatg aacttcggtg aaaaaccgca gcagggaggc    1800
aaacaatga                                                             1809
```

<210> SEQ ID NO 32
<211> LENGTH: 5742
<212> TYPE: DNA

<213> ORGANISM: Artificial sequence
<220> FEATURE:
<223> OTHER INFORMATION: Pseudomonas fluorescens tryptophan halogenase
    PrnA (prnA), PrnB (prnB), halogenase PrnC (prnC) and
    aminopyrrolnitrin oxidase PrnD (prnD) genes

<400> SEQUENCE: 32

```
atgaacaagc caatcaagaa tatcgtcatc gtgggcggcg gcaccgcggg ctggatggcc      60
gcttcgtacc tcgtccgggc gctccaacag caggtaaaca tcacgctcat cgagtctgcg     120
gcgatccccc ggatcggcgt gggcgaggcg accatcccga gtttgcagaa ggtgttcttc     180
gacttcctcg gataccgga gcgggagtgg atgccccaag tgaacggcgc cttcaaggcc     240
gcgatcaagt tcgtgaactg agaaaatct cccgacccat cgcgcgaaga ttacttctac     300
catttgttcg gcagcgtgcc gaactgcgac ggcgtgccgc ttacccacta ctggctcgcc     360
aagcgcgaac agggcttcca gcagccgatg gcgtacgcgt gctatccgca gcccggggcc     420
ctcgacggca gctggcaccc tgcctggcc gacggcaccc gccagatgtc ccacgcgtgg     480
cacttcgacg cgcacctggt ggccgacttc ttgaagcgct gggccgtcga gcgcggggtg     540
aatcgcgtgg tcgacgaggt cgtggaggtt caactgaacg accgcggcta catctccacc     600
ctgttaacca aggaagggcg gacgctggag gcggacctgt catcgactg ctccggcatg     660
cgagggctcc tgatcaatca ggccctgaag gaaccettca tcgacatgtc cgactacctg     720
ctgtgcgaca gcgcggtcgc cagcgccgtg cccaacgacg acgcgcgcga ggggtcgag     780
ccttacacct ccgcgattgc catgaactcg gatggacct ggaagattcc gatgctgggc     840
cggttcggca gcggctacgt cttctcgagc aagttcacct cgcgcgacca ggccaccgcc     900
gacttcctca aactctgggg cctctcggac aatcagcagc tcaaccagat caagttccgg     960
gtcgggcgca acaagcgggc gtgggtcaac aactgcgtct cgatcgggct gtcgtcgtgc    1020
tttctggagc ccctggaatc gacgggaatc tacttcatct acgcggcgct ttaccaactc    1080
gtgaagcact tccccgacac ctcgttcgac ccgcggttgc gcgacgcatt caacgccgag    1140
atcgtctaca tgttcgacga ctgccgagac ttcgtccagg cgcactattt cactacgtcg    1200
ccgcgaagaca cgccgttctg gctcgcgaac cggcacgaac tgcggctctc ggacgccatc    1260
caggagaagg ttgagcgcta caaggccggg ctgccactga ccaccacctc gttcgacgat    1320
tccacgtact acgagacctt cgactacgaa ttcaagaact tctggttgaa cggcaactac    1380
tactgcatct ttgccggcct gggcatgctg cccgaccggt cgctgccgct cctgcagcac    1440
cgaccggagt cgatccagaa ggccgaagcg atgttcgcca gcatccggcg cgaagccgag    1500
cgcctgcgca cgagcctgcc gacgaactac gactacctgc ggtcactgcg tgacggcgcg    1560
cagctgtcgc gcaaccagca cgggccgacg ctcgcggctc aggaacgcca gtagtggaac    1620
gcaccttgaa ccgggtatcc gcattcgcgg ccacacacgc tgccgtggcg gcctgcgatc    1680
cgctacaggc acgcgcgctg gttctgcagc tgccggccct gaaccgtgac aaggacgtgc    1740
ccggcatcgt cggcctgctg cgcgattccc tcccggtgag cggcgtgccc tccagctggg    1800
gcttcgtcga agccgccgcc gcgatgcggg acatcggttt cttcctgggg tcgctcaagc    1860
ggcacggaca tgagcccgtg gacctggtgc ccgggcttga acgggtgctg ctcgacctgg    1920
cacgggtgac cgacttgccg ccgcgcgaga cactcctgca tgtgacgtc tggaacccgg    1980
cggcggccga tgcgcagcgg agctacaccg ggctgcccga cgaagcgcac ctgctcgaga    2040
gcgtgcgcat tcgatggcg gccctcgagg cggccatcgc gttgaccgtc gagctgtccg    2100
atgtatccct gcgctcgccc gcgttcgcgc aagggtgcga tgagctggaa gcctacctgc    2160
```

```
agaaaatggt cgaatcgatc gtctacgcgt accgcttcat ctcgcccag gtcttctacg    2220 atgagctgcg ccccttctac gaaccgattc gagtcggggg ccagagctac ctcggccccg    2280
gcgccgtaga aatgcccctc ttcgtgctgg agcacgtcct gtggggctcg caatcggacg    2340
acccagctta tcgagaattc aaagagacat acctgcccta cgtgcttccc gcgtacaggg    2400
cggtctacgc tcggttcgcc acaaagccgg cgctcatcga ccgtgcgctc gacgaggcgc    2460
gagcggtggg tacgcagggc gagcacgtcc gggctgggct gacggccctc gagcgggtct    2520
tcaaggtcct gctgcgcttc cgggcgcctc acctcaaatt ggcggagcgg gcatacgaag    2580
ccgggcgcag cggccccaca accggcagcg ggggctacgc gcccagcatg ctcggcgatc    2640
tactcacgct cacctgtgcc gcgcggtccc gcatccgtgc cgcgctcgat gaatcctgat    2700
gcgcgcgacc cagtgttatc tcacaaggag agtttgcccc catgactcag aagagccccg    2760
cgaacggaca cgatagcaac cacttcgacg taatcatcct cggttcgggc atgtccggta    2820
cccagatggg ggccatcctg gccaaacaac agtttgcgt gctgatcatc gagcagtcgt    2880
cgcacccgcg gttcacgatc ggcgaatcgt cgatcccga aacgtctctc atgaaccgca    2940
tcatcgctga tcgctacgac attccggagc tcggccacat cacctcgttc tactcgacgc    3000
agcgttacgt ttcgtcgagc acgggcatca agcgcaactt cggcttcgtg ttccacaaac    3060
ctggccagga gcacgacccg aaggagttca cccagtgcgt cattcccgag ctgccgtggg    3120
ggccggagag ccattattac cggcaggacg tcgacgccta tctgttgcaa gcggccatca    3180
aatatggctg cacggtccgc cagaagacga gcgtgaccga atatcacgcg gacaaggacg    3240
gcgtcgcggt gaccaccgcc gagggcgagc ggttcaccgg ccggtacatg atcgactgcg    3300
gaggacccgg cgcgccgctg gcgaccaagt tcgggctccg cgaagagccg tgtcgcttca    3360
agacgcactc gcgcagcctc tacacgcaca tgctcggggt caagccgttc gacgcatct    3420 tcaaggtcaa ggggcagcgc tggcgctggc acgaaggaac cctgcaccac atgttcaccg    3480
gcggctggct ctgggtgatt ccgttcaaca accaccgcg ctcgaccaat aacctggtga    3540
gcgtcggcct gcagctcgac ccgcgtgtct acccgaaaac cgacattccc gcgcagcagg    3600
aattcgacga gttcctcgcg cggttcccga gcatcggcgc tcagttccgg gacgccgtgc    3660
cagtgcgcga ctgggtcaag accgaccgcc tgcagttctc gtcgaacgcc tgcgtcggcg    3720
accgctactg cctgatgctg cacgcgaacg ggttcatcga cccgctcttc tcccgggggc    3780
tcgagaacac cgcggtgacc atccacgcgc tcgcggcgcg cctcatcaag gcgctacgcg    3840
acgacgactt ctcccccgag cgcttcgagt acatcgagcg cctgcagcaa aagcttttgg    3900
accacaacga cgacttcgtc agctgctgct acacggcgtt ctcggacttc cgcctatggg    3960
acgcgttcca ccgctgtgg gcggtcggca ctatcctcgg gcagttccgg ctggtgcaag    4020
cccacgcgag gtttcgcgcg tcgcgcgacg agggcgacct cgatcacctc gacaacgacc    4080
cgccgtacct cgggtacctg tgcgcggaca tggagcagta ctaccagttg ttcaacgacg    4140
ccaaagccga ggtcgaggct gtgagcgccg ggcacaagtc ggccgaggag ccgcgttgc    4200 ggattcacgc cctcatcgac gaacgagact tcgccaagcc gatgttcggc ttcgggtact    4260
gcatcaccgg ggacaagccg cagctcaaca actcgaagta cagcctgata ccggcgatga    4320
agctgatgta ctggacgcaa acccgcgcgc cggcagaggt gaagaagtac ttcgactaca    4380
acccgatgtt cgcgctgctc aaggcgtaca tcaccacccg catcggcttg gctctgaaga    4440
agtagtcggc caaggacggc acacacgcga tgaacaacat tcaattggat caagcgaacg    4500
tcaagaagca tcccccgggg gcgtacgacg cgaccacacg cgtggccgcg agctggtacg    4560
```

```
tcgcgatgcg ctcgaacggc ctcagggaca agccgaagga gttgacgctc tttggccgtc      4620
cgtacgtggc gtggcgcgca gcgacggggc aggccgtggt gatggaccgc cactgctcgc      4680
acctgggcgc gaacctggct gacgggcgga tcaaggacgg gtgcatccag tgcccgtttc      4740
accactggcg ctacgacgag caaggcaagt gcgttcacat ccccggccac agcgaggtgg      4800
tgcgccagct ggagccggtg ccacgcgcgg cgcgccagcc gacgttggtc accaccgagc      4860
gatacggcta cgtgtgggtc tggtacggct ccccgcagcc gctgcacccg ctgcccgaaa      4920
tcaccgcagc cgacgtcgac aacggcgact tcatgcacct gcacttcgcg ttcgagacga      4980
cgacggcggt cttgcggatc gtcgagaact tctacgacgc acagcacgca accccgtgc       5040 acgcgctccc gatctcggcc ttcgaactca agctcttcga cgactggagc cggtggccgg      5100
aggttgagtc gctggcccgg gcgggcgcgt ggttcggtgc cgggatcgac ttccacgtga      5160
accgctactt cggcccccctc ggcatgctgt cgcgcgcgct cggcctgaac atgtcgcaga     5220
tgaacctgca cttcgatggc taccccggcg ggtgcgtcat gaccgttgcc ctggacgcag      5280
acgtcaaata caaactgctc cagtgtgtga caccggtgag cgacggcaag aacatcatgc      5340
acatgctcat ctcgatcaag aaggtgggcg gcgtcctgcg ccgtgcgacc gacttcgtgc      5400
tgttcgggct gcagaccaga caggcagcgg ggtacgacgt caaaatctgg aacgggatga      5460
agcccgacgg cggcggcgct tacagcaagt acgacaagct cgtgctcaag taccgtgcgt      5520
tctaccgcgg ctgggtcgac cgtgtcgcga gtgagcagta atgcgtgagg ccgagccggt      5580
agcggtcgcg tcgcgctgcc cggcgcttgc gaacctttcg agctgcgtca cggagatcac      5640
ggcgtacggc gcggcgggcc cgcttgggct cgcggccacc cgcttggtgt cggtgtcgct      5700
ctttgcgagg tattgatgac catctggctg ttgcaactcg tg                         5742
```

<210> SEQ ID NO 33
<211> LENGTH: 10
<212> TYPE: PRT
<213> ORGANISM: Tomato yellow leaf curl virus
<220> FEATURE:
<221> NAME/KEY: misc_feature
<223> OTHER INFORMATION: Partial sequence of the TYLCV coat protein

<400> SEQUENCE: 33

Gly Cys Glu Gly Pro Cys Lys Val Gln Ser
1               5                   10

<210> SEQ ID NO 34
<211> LENGTH: 717
<212> TYPE: DNA
<213> ORGANISM: Artificial sequence
<220> FEATURE:
<223> OTHER INFORMATION: V1 (coat protein) (717 bp, including "TAA" STOP
      codon) coding polynucleotide

<400> SEQUENCE: 34

```
atgtcgaagc gaccaggcga tataatcatt tccacgcccg tctcgaaggt tcgccgaagg       60
ctgaacttcg acagcccata caggcccatg taccgaaagc ccagaatata cagaatgtat      120
cgaagccctg atgttccccg tggatgtgaa ggccatgta  aagtccagtc ttatgagcaa      180
cgggatgata ttaagcatac tggtattgtt cgttgtgtta gtgatgttac tcgtggatct      240
ggaattactc acagagtggg taagaggttc tgtgttaaat cgatatattt tttaggtaaa      300
gtctggatgg atgaaaatat caagaagcag aatcacacta atcaggtcat gttcttcttg      360
gtccgtgata gaaggcccta tggaaacagc ccaatggatt ttggacaggt ttttaatatg      420
ttcgataatg agcccagtac cgcaaccgtg aagaatgatt tgcgtgatag gtttcaagtg      480
```

```
atgaggaaat tcatgctac agttattggt gggccctctg gaatgaagga acaggcatta    540
gttaagagat tttttaaaat taacagtcat gtaacttata atcatcagga ggcagcaaag    600
tacgagaacc atactgaaaa cgccttgtta ttgtatatgg catgtacgca tgcctctaat    660
ccagtgtatg caactatgaa aatacgcatc tatttctatg attcaatatc aaattaa      717
```

<210> SEQ ID NO 35
<211> LENGTH: 313
<212> TYPE: DNA
<213> ORGANISM: Artificial sequence
<220> FEATURE:
<223> OTHER INFORMATION: IR coding polynucleotide

<400> SEQUENCE: 35

```
gttgaaatga atcggtgtct ctcaaagctc tatggcaatc ggtgtatcgg tgtcttactt     60
atacctggac acctaatggc tatttggtaa tttcataaat gttcattgca attcaaaatt    120
caaaattcaa aaatcaaatc tttaaagcgg ccatccgtat aatattaccg gatggccgcg    180
ccttttgttt ttatgtggtc cccacgaggg ttacacagac gtcactgtca accaatcaaa    240
ttgcattctc aaacgttaga taagtgttca tttgtcttta tacttggt ccccaagttt     300 tttgtcttgc aat                                                       313
```

<210> SEQ ID NO 36
<211> LENGTH: 287
<212> TYPE: DNA
<213> ORGANISM: Artificial sequence
<220> FEATURE:
<223> OTHER INFORMATION: C1 (trancated) and C2 (truncated) coding
      sequence

<400> SEQUENCE: 36

```
gttgagctct tagctgcctg aatgttcgga tggaaatgtg ctgacctgtt tggtgatacc     60
aggtcgaaga accgttggtt cttacattgg tatttgcctt cgaattggat aagcacatgg    120
agatgtggtt ccccattctc gtggagttct ctgcaaactt tgatgtattt tttatttgtt    180
ggggtttcta ggttttttaa ttgggaaagt gcttcctctt tagagagaga acaattggga    240
tatgttagga ataatttttt ggcatatatt ttaaataaac gaggcat                  287
```

<210> SEQ ID NO 37
<211> LENGTH: 291
<212> TYPE: DNA
<213> ORGANISM: Artificial sequence
<220> FEATURE:
<223> OTHER INFORMATION: V2 coding sequence

<400> SEQUENCE: 37

```
atgtgggacc cacttcttaa tgaatttcct gaatctgttc acggatttcg ttgtatgtta     60
gctattaaat atttgcagtc cgttgaggaa acttacgagc ccaatacatt gggccacgat    120
ttaattaggg atcttatatc tgttgtaagg gcccgtgact atgtcgaagc gaccaggcga    180
tataatcatt tccacgcccg tctcgaaggt tcgccgaagg ctgaacttcg acagcccata    240
caggcccatg taccgaaagc ccagaatata cagaatgtat cgaagccctg a             291
```

<210> SEQ ID NO 38
<211> LENGTH: 45
<212> TYPE: PRT
<213> ORGANISM: Artificial sequence
<220> FEATURE:
<223> OTHER INFORMATION: Truncated C2 polypeptide

```
<400> SEQUENCE: 38

Met Gly Asn His Ile Ser Met Cys Leu Ser Asn Ser Lys Ala Asn Thr
1               5                   10                  15

Asn Val Arg Thr Asn Gly Ser Ser Thr Trp Tyr His Gln Thr Gly Gln
                20                  25                  30

His Ile Ser Ile Arg Thr Phe Arg Gln Leu Arg Ala Gln
            35              40                  45
```

PLANT EXPRESSION CONSTRUCTS COMPRISING AND USES THEREOF

CROSS-REFERENCE TO RELATED APPLICATION

This application is a 371 of PCT Patent Application No. PCT/IL2009/00682 filed Jul. 8, 2009 which claims the benefit of priority of U.S. Provisional Patent Application Ser. No. 61/129,596 filed Jul. 8, 2008.

SEQUENCE LISTING

The text file is SEQUENCE_LISTING, created Jan. 4, 2011, and of size 60 KB, filed therewith, is hereby incorporated by reference.

FIELD AND BACKGROUND OF THE INVENTION

The present invention, in some embodiments thereof, relates to Gemini-virus constructs capable of symptomless, systemic spread in plant hosts.

Plants may be genetically engineered for a variety of purposes including for the generation of plants with enhanced viral resistance, for the development of abiotic stress tolerant plants, for commercially improved plants and for the expression of heterologous polypeptides for pharmaceutical and industrial purposes.

Present techniques for DNA delivery into plants include direct as well as indirect methods. However, each of these delivery methods is not without limitations. The direct DNA delivery systems such as particle bombardment, silicon carbide whisker technology and electroporation tend to result in integration of multiple copies of transgenes and are considered to be limited, unpredictable and transient. Indirect approaches such as *Agrobacterium* oftentimes result in integration of multiple copies of the foreign DNA into the plant genome along with unwanted sequences from the vector 'backbone'.

Integration of foreign DNA into the plant genome to become a heritable trait raises many risks. Traits beneficial to crops may, through horizontal gene transfer or hybridization through breeding with wild relatives, provide wild plants with unwanted competitive advantages. Also, Transformation with *Agrobacterium* is a complex process which requires elimination of false positives arising from the growth of *Agrobacterium* in host tissues, and selection of transformed plants. The use of antibiotic resistance as a marker in the development of transgenic crops has also raised concerns regarding the increase of antibiotic resistance in the environment through horizontal transfer of antibiotic resistance genes to soil micro-organisms. Scientists now have the means to remove marker genes before a crop plant is developed for commercial use, but these means involve further costs and tedious procedures. In addition, several species or varieties of plants are still difficult to transform.

Infection of plants with modified viruses is simpler and quicker than the regeneration of stably transformed plants, since plant viruses are small and easy to manipulate, have the inherent ability to enter the plant cell, and will multiply to produce a high copy number of the gene of interest. Viral vectors have been engineered for delivery of genetic material and expression of recombinant proteins in plants. Viral expression systems are considered transient expression systems since the viral vectors are not integrated into the genome of the host. However, viral vectors still hold many limitations.

Plant viral vectors have the potential to cause disease in their plant hosts, they posses the ability to naturally spread between plants in the field, and in some cases, can be spread through pollen or seed to the next generation. Viral vectors are also limited in their systemic spread in the plant, in host ranges, expression stability, and in the size of insert which can be tolerated. Finally, like transgenic plants, modified viruses are classified as a Genetically Modified Organism (GMO) and thus are subject to regulatory and moral constraints.

Viruses belonging to the family Geminiviridae carry one or two circular single-stranded (ss) DNA genomes and are insect-transmissible. Begomoviruses, Curtoviruses, Mastreviruses and Topocuviruses are genera within this family which have been classified according to genome organization, insect transmissibility and host range. Begomoviruses can carry a monopartite or bipartite genome and are whitefly-transmissible. The association of satellite DNAs with monopartite begomoviruses is addressed further on.

Tomato yellow leaf curl virus (TYLCV) is a monopartite begomovirus. It carries six overlapping open reading frames (ORFs) transcribed bi-directionally from an intergenic region (IR; also termed "common region"), serving as the viral origin of replication and as a bi-directional promoter. The IR is about 300-bp long and carries the universal motif TAATATT/AC and a binding site for the replicase-associated protein (REP). Two ORFs are expressed in viral orientation (V1, V2) and four ORFs in the complementary orientation (C1 to C4). Each gene product appears to participate in more than one function. The viral ssDNA is transmitted to the plant and converted into double-stranded (ds) DNA (replicative form) by the host machinery. The dsDNA replicates and expresses viral mRNAs and proteins. Viral genes are not involved in this stage of replication (dsDNA to dsDNA). However, when rolling circle replication (RCR) is initiated by REP, RCR intermediates may serve as templates for dsDNA replication, dependent on host gene activity. At the next stage of replication, the numerous viral dsDNAs serve as templates for RCR, producing progeny ssDNA. ORF C1 (also termed rep) is essential for the initiation of RCR. The progeny ssDNA molecules are then encapsidated, transported to other tissues or transmitted to other plants. At least three viral gene products are implicated in viral movement within the plant: V2, the coat protein (CP) V1, and C4. The viral genes V1, V2, C4 and probably C2 are implicated in symptom appearance and disease severity. In summary, five of the viral ORFs have no direct role in viral DNA replication or expression (some have auxiliary roles), whereas the sixth ORF (rep) is involved only in the rolling-circle phase. Movement and pathogenicity, however, require the activity of viral gene products.

The association of viral satellites with RNA viruses is a well-documented phenomenon. Satellites, either encapsidated or in the form of naked nucleic acid, depend on a helper virus for their replication. A geminivirus-associated, 682-base-long DNA satellite was first reported by Dry et al. in 1997, Proc. Natl. Acad. Sci. USA 94, 7088-7093. This satellite was associated with an Australian type of TYLCV and did not share sequence homology with the helper virus. However, the satellite carried two motifs that also reside in the IR of the helper virus: the universal stem-loop motif and the REP-binding motif. Other gemini-associated satellites have been discovered since then (Briddon et al., 2001, Virology 285, 234-243; Mansoor et al., 1999, Virology 259, 190-199; Zhou et al., 2003, J. Gen. Virol. 84, 237-247. All of these satellite DNAs (generally referred to as DNAβ and DNA-1) are about half the size of the viral DNA, and carry, in addition to the aforementioned motifs, an ORF termed βC1. The role of the putative βC1 protein has not yet been conclusively determined but it is probably involved in movement, nuclear localization and silencing suppression (Cui et al., 2005, J. Virol. 79, 10764-10775). In many cases of geminiviral infection, the satellite determines symptom severity. Geminiviral satellites are encapsidated and replicated via factors provided by helper viruses. A satellite associated with a particular virus may be supported for replication by other geminiviruses as well.

International Patent Application WO2007/141790 teaches Gemini-virus based constructs wherein the inserted sequence to be expressed is flanked by a non-contiguous nucleic acid sequence encoding a Geminivirus replicase.

SUMMARY OF THE INVENTION

According to an aspect of some embodiments of the present invention there is provided a method of expressing a molecule of interest in a plant, the method comprising contacting roots of the plant in a solution comprising at least one Geminivirus based expression construct so as to allow the at least one Geminivirus based expression construct to be absorbed by the roots, the expression construct comprising a polynucleotide encoding the molecule of interest, and further the expression construct being capable of systemic symptomless spread in a plant host, thereby expressing a molecule of interest in a plant.

According to an aspect of some embodiments of the present invention there is provided a method of expressing a molecule of interest in a plant, the method comprising grafting a section of a first plant infected with at least one Geminivirus based expression construct onto a section of a second plant, the expression construct comprising a polynucleotide sequence which encodes the molecule of interest, and further the Geminivirus based expression construct being capable of systemic symptomless spread in a plant host, thereby expressing a molecule of interest in a plant.

According to some embodiments of the invention, the Geminivirus based expression construct is devoid of a polynucleotide sequence encoding a C2 and C3 coding sequence.

According to some embodiments of the invention, the Geminivirus based expression construct comprises a polynucleotide sequence encoding the molecule of interest, the polynucleotide sequence being flanked by a non-contiguous nucleic acid sequence encoding a Geminivirus replicase.

According to an aspect of some embodiments of the present invention there is provided a Geminivirus based expression construct, capable of systemic symptomless spread in a plant host, the expression construct being devoid of a polynucleotide sequence encoding a C2 and C3 coding sequence.

According to an aspect of some embodiments of the present invention there is provided a method of expressing a molecule of interest in a plant cell comprising introducing into the plant tissue the nucleic acid construct the present invention, the heterologous polypeptide being the molecule of interest, thereby expressing a molecule of interest in a plant cell.

According to some embodiments of the invention, the expression construct comprises:
a polynucleotide sequence encoding a Geminivirus intergenic region (IR);
(ii) a polynucleotide sequence encoding a modified Geminivirus coat protein (CP); and
(iii) a polynucleotide sequence encoding a modified Geminivirus precoat protein (V2).

According to some embodiments of the invention, the expression construct further comprises a polynucleotide sequence encoding a modified replicase protein (C1).

According to some embodiments of the invention, the modified replicase protein is as set forth in SEQ ID NO: 36.

According to some embodiments of the invention, the expression construct further comprises a polynucleotide sequence encoding a modified C4 protein.

According to some embodiments of the invention, the expression construct is capable of replication in a prokaryotic cell.

According to some embodiments of the invention, the expression construct is incapable of plant to plant transmission by an insect vector.

According to some embodiments of the invention, the expression construct further comprises a heterologous polynucleotide sequence.

According to some embodiments of the invention, the heterologous polynucleotide is larger than 1 kb.

According to some embodiments of the invention, the heterologous polynucleotide is larger than 5 kb.

According to some embodiments of the invention, the heterologous polynucleotide comprises an operon.

According to some embodiments of the invention, the heterologous polynucleotide is adapted for gene silencing.

According to some embodiments of the invention, the expression construct comprises a bacterial polynucleotide sequence.

According to some embodiments of the invention, the modified Geminivirus V2 protein is as set forth in SEQ ID NO: 6.

According to some embodiments of the invention, the modified Geminivirus coat protein comprises an amino acid sequence as set forth in SEQ ID NO: 3.

According to some embodiments of the invention, the modified Geminivirus coat protein comprises a mutation or deletion in nucleotides encoding an N-terminal 100 amino acids.

According to some embodiments of the invention, the expression construct comprises a polynucleotide sequence as set forth in SEQ ID NO: 10 or 11.

According to some embodiments of the invention, the heterologous polynucleotide encodes a polypeptide selected from the group consisting of a reporter molecule, an antiviral molecule, a viral moiety, an antifungal molecule, an antibacterial molecule, an insect resistance molecule, a herbicide resistance molecule, a biotic or abiotic stress tolerance molecule, a pharmaceutical molecule, a growth inducing molecule, and a growth inhibiting molecule.

According to some embodiments of the invention, the Geminivirus is a begomovirus.

According to some embodiments of the invention, the Geminivirus is a Tomato yellow leaf curl virus (TYLCV).

According to some embodiments of the invention, the expression construct is adapted for expression in a plant host selected from the group consisting of Solanaceae, Cucurbitaceae, Umbelliferae, Liliacae, Gramineae (Poaceae), Rosaceae, Musaceae, Vitacea, and Cruciferae.

According to some embodiments of the invention, the molecule of interest is selected from the group consisting of a reporter molecule, an antiviral molecule, a viral moiety, an antifungal molecule, an antibacterial molecule, an insect resistance molecule, a herbicide resistance molecule, a biotic or abiotic stress tolerance molecule, a pharmaceutical molecule, a growth inducing molecule, a product of genes in a metabolic pathway and a growth inhibiting molecule.

According to some embodiments of the invention, the genes in the metabolic pathway are encoded by an operon.

According to some embodiments of the invention, the plant is selected from the group consisting of a Solanaceae, a Cucurbitaceae, an Umbelliferae, a Liliacae, a Gramineae (Poaceae), a Rosaceae Musaceae, Vitacea and a Cruciferae.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C are schematic representations of the constructs IR-V2-CP (FIG. 1A), IR-V2-CP-GFP (FIG. 1B) and IR-GUS.

FIG. 2A: negative control—untreated plants, FIG. 2B: Plants treated with IR-GFP only, FIG. 2C-F: Plants treated with IR-V2-CP-GFP.

FIGS. 3A-B are images illustrating the IR-V2-CP requirement for in-trans replication and movement of another satellite. FIG. 3A: IR-GUS was injected into plants along with IR-V2-CP. FIG. 3B: a control plant injected with IR-GUS only.

FIGS. 3C-F are photographs of ethidium bromide stained gels. FIG. 3C: PCR analysis of DNA from plants treated with IR-V2-CP-GFP with TYLCV-CP primers. Lanes 2, 4, 6, 8: negative controls; DNA extracted from untreated plants. Lanes 3, 5, 7, 9: analysis of DNA from remote leaves of plants injected with IR-V2-CP-GFP. FIG. 3D: Detection of TYLCV-CP transcripts by RT-PCR in plants treated with IR-V2-CP-GFP. Lanes 2, 4, 6: RT-PCR was carried out with RNA template from various plants injected with IR-V2-CP-GFP. Lanes 3, 5, 7: same reactions carried out with the same RNA templates without reverse transcriptase. FIG. 3E: PCR analysis of plants with GFP primers. Lanes 2, 5: plants were injected with IR-V2-CP-GFP. Lanes 3, 4: DNA was extracted from untreated plants. FIG. 3F: PCR assays to rule out the presence of TYLCV in IR-V2-CP-GFP-injected plants. PCR was conducted with primers for TYLCV CP (product should appear in plasmid-treated and virus-infected plants) and with primers for TYLCV C2 (product should appear only in TYLCV-infected plants). Lane 6: negative control; PCR was conducted with DNA from untreated plants. Size markers are shown in the leftmost lane in FIGS. 3C-F.

FIG. 4 is a photograph of an ethidium bromide stained gel demonstrating the results of PCR analysis for GUS in rootstocks which had been grafted with scions carrying IL-60-BS+IR-GUS. Lanes 1 to 3: Different grafted tobacco plants. Lanes 4 to 6: Different grafted tomato plants. Lane 7: Negative control (no template). Lane 8: Size markers.

DESCRIPTION OF SPECIFIC EMBODIMENTS OF THE INVENTION

Figure 2A:
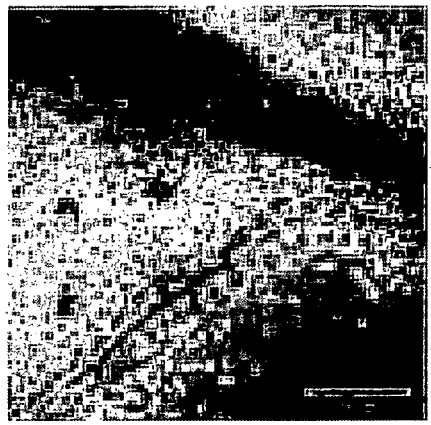
FIGS. 2A-F are images illustrating the replication and movement of IR-V2-CP-GFP in tomato plants.
Figure 2B:

The present invention, in some embodiments thereof, relates to Gemini-virus constructs capable of symptomless, systemic spread in plant hosts and methods of expressing molecules of interest using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Tomato yellow leaf curl virus (TYLCV) is a monopartite begomovirus. It carries six overlapping open reading frames (ORFs) transcribed bi-directionally from an intergenic region (IR; also termed "common region"), serving as the viral origin of replication and as a bi-directional promoter. The IR is about 300-bp long and carries the universal motif TAATATT/AC [SEQ ID NO: 9] and a binding site for the replicase-associated protein (REP). Two ORFs are expressed in viral orientation (V1, V2) and four ORFs in the complementary orientation (C1 to C4).

Whilst analyzing the relevance of the genes of the TYLCV, the present inventors found that the virally oriented (sense) genes V1 and V2, together with the viral integration region (IR), were sufficient for the virus's dsDNA replication (dsDNA to dsDNA), its mobilization throughout the plant and the expression of its genes. This was particularly surprising in light of the fact that mutations in C4 were previously shown to result in lack of systemic spread and reduce levels of virus in tomato plants, and C4 was therefore considered to be associated with movement (Jupin et al. (1994) Virology 204, 82-90).

However, the present inventors found that a 1486-bp IR-V2-CP fragment, devoid of functional C1, C2, C3 and C4, was able to promote DNA replication and mobilization, but to exclude the rolling-circle phase of replication. Accordingly, this fragment prevented synthesis of single-stranded (ss) DNA. Consequently, replication, mobilization and expression occurred without causing disease symptoms.

Whilst reducing the present invention to practice, the present inventors showed that this construct could be used to express foreign DNA in a plant (FIGS. 2A-F and 3C-F). The present inventors further showed that this construct could be used to aid in replication and movement of another geminivirus based satellite (FIGS. 3A-B).

In addition, the present inventors discovered that geminivirus based expression vectors which are capable of systemic symptomless spread in a plant host are capable of being absorbed into a plant via its roots (FIGS. 5 and 6) or transferred from one plant to another via grafting (FIG. 4).

Thus, according to one aspect of the present invention there is provided a Geminivirus based expression construct, capable of systemic symptomless spread in a plant host, the expression construct being devoid of a polynucleotide sequence encoding a C2 and C3 coding sequence.

As used herein, the phrase "systemic symptomless spread" refers to the ability of the plant virus-based vector of the present invention to spread, for example, into leaves not serving as the site of infection without inducing the characteristic geminivirus symptoms such as leaf yellowing, leaf curling, stunting of plant growth, or development of flowers or fruit.

Examples of susceptible host species include *Cynanchum acutum, Datura stramonium, Hyoscyamus desertorum, Lens culinaris, Lycopersicon esculentum, Lycopersicon pimpinellifolium, Malva nicaensis, Malva parviflora, Nicotiana benthamiana, Nicotiana glutinosa, Nicotiana tabacum, Phaseolus vulgaris* and *Sonchus oleraceus*, as well as insusceptible host species such as *Abelmoschus esculentus, Althaea rosea, Amaranthus retroflexus, Arachis hypogaea, Atriplex, Beta vulgaris, Calotropis aegyptia, Capparis aegyptia, Chenopodium amaranticolor, Cucumis sativus, Gomphrena globosa, Gossypium hirsutum, Hibiscus rosa-sinensis, Lavatera cretica, Lonicera, Lycium, Medicago sativa, Momordica balsamina, Nerium oleander, Nicotiana rustica, Ochradenus baccatus, Physalis floridana, Pisum sativum, Plumbago capensis, Polygonum equisetiforme, Portulaca oleracea, Prosopis farcta, Ricinus communis, Solanum incanum, Solanum villosum, Tamarix, Tribulus, Vicia faba, Withania somnifera, Xanthium strumarium* and *Zinnia elegans*.

Additional susceptible and insusceptible hosts are listed in http://pheneDOTcpmcDOTcolumbiaDOTedu/ICTVdB/ 29030000.htm Preferred Geminiviruses which can be used with the present invention include the tomato yellow leaf curl virus (TYLCV) as well as other Begomoviruses (see, pheneDOTcpmcDOTcolumbia.edu/ICTVdB/29030000.htm). It will be appreciated that although some of the terminology utilized herein refers to the genes encoded by TYLCV, one of ordinary skill in the art would be more than capable of identifying and utilizing the genetic orthologues of other geminivirus species and strains.

As mentioned, the nucleic acid constructs of the present invention are devoid of functional C1, C2, C3 and C4 coding sequences. According to one embodiment, the construct is devoid of C2 and C3 coding sequences.

According to one embodiment, the nucleic acid construct of the present invention comprises modifications in the C1 and C4 genes. These modifications may be conservative or non-conservative.

According to one embodiment of this aspect of the present invention, the modifications in the C1 and C4 genes are such that the proteins encoded by same are non-functioning. Thus, the modification may be a truncation, a point mutation, a frame shift mutation, a partial deletion or a full deletion.

Accordingly, the present invention contemplates a construct which comprises a truncated C1 sequence (SEQ ID NO: 36) and a truncated C4 sequence (SEQ ID NO: 38) and is devoid of C2 and C3 completely.

According to another embodiment of this aspect of the present invention, the nucleic acid construct of the present invention comprises modifications in the V1 gene (encoding the coat protein (CP)) and/or the V2 (encoding the precoat protein) gene.

For example, the part of the CP that is involved in viral movement and systemic spread in plants has been mapped to the C-terminal part of the CP (Noris. et. al. (1998) J. Virol. 72, 10050-10057). Accordingly, the present invention contemplates altering the N-terminal part of the CP in some cases. In an exemplary embodiment of the invention, 60 nucleotides (corresponding to positions 552-612) of the TYLCV may be deleted, causing the removal of 20 amino acids (positions 27 to 46) from the native viral CP. The resultant CP would still carry a bipartite nuclear-localization signal (NLS; amino acids 1-20), although a third part (KRR at position 41-43) of what may have been a tripartite NLS would be removed.

According to one embodiment, the sequence of the CP is as set forth in SEQ ID NO: 34.

Alternatively, or additionally, point mutations may be introduced by single-base deletion into the V2 gene. For example, a single-base deletion may be introduced at position 640 of the native TYLCV-DNA, causing a frameshift which may be corrected for—for example by adding a G to position 744 of the native viral DNA. Due to the resultant frameshift, a stretch of amino acids residing between positions 56 and 91 of the native CP would become different, with no apparent similarity to the corresponding stretch (positions 926 to 1031) of IR-V2-CP. Beyond that point, however, the CP sequences of TYLCV and IR-V2-CP would be almost identical. Due to the changes in amino acids 56 to 91, the conserved sequence GCEGPCKVQS (SEQ ID NO: 33), carried by all geminiviruses tested to date (Kirthi et al. (2003) Arch. Virol. 148, 2369-2380), would be missing from IR-V2-CP. In many viruses (but not TYLCV), this sequence is part of a zinc-finger motif required for attachment to single-stranded (ss) DNA (apparently for encapsidation), a property that is redundant for a vector.

Deletion at the N terminus of the CP typically results in a deletion at the C terminus of the overlapping ORF V2 ("precoat"). Thus, for example, the present invention contemplates constructs comprising a V2 gene as set forth in SEQ ID NO: 37, encoding the polypeptide sequence as set forth in SEQ ID NO: 6.

It will be appreciated that in order for the expression construct of the present invention to be expressed, the expression construct typically comprises an IR region. This region serves, amongst other things as a bi-directional promoter.

The IR derived sequence can include for example, a nucleotide region defined by coordinates 1-314 or 62-314 of TYLCV (GenBank Accession number X15656). For example, the IR derived sequence may be set forth in SEQ ID NO: 35.

The present invention also contemplates modifications in the IR region. Typically, these modifications do not affect the promoter region or the ability of the IR to direct expression in a plant over an extended period of time in the plant (e.g. longer than one month, 3 months, 6 months 1 year or even over the entire lifetime of the plant).

One example of an IR region which can be targeted for modification is the replication-associated protein binding domain (Akbar Behjatnia et al. Nucleic Acids Research, 1998, Vol. 26, No. 4, 925-931).

The aforedescribed alterations are all consistent with a disarmed dsDNA construct which is capable of replicating (dsDNA to dsDNA) by attracting the host machinery to its origin of replication and retaining its mobility, but with no ability to produce progeny viral ssDNA.

Figures 1A, 1B, 1C:
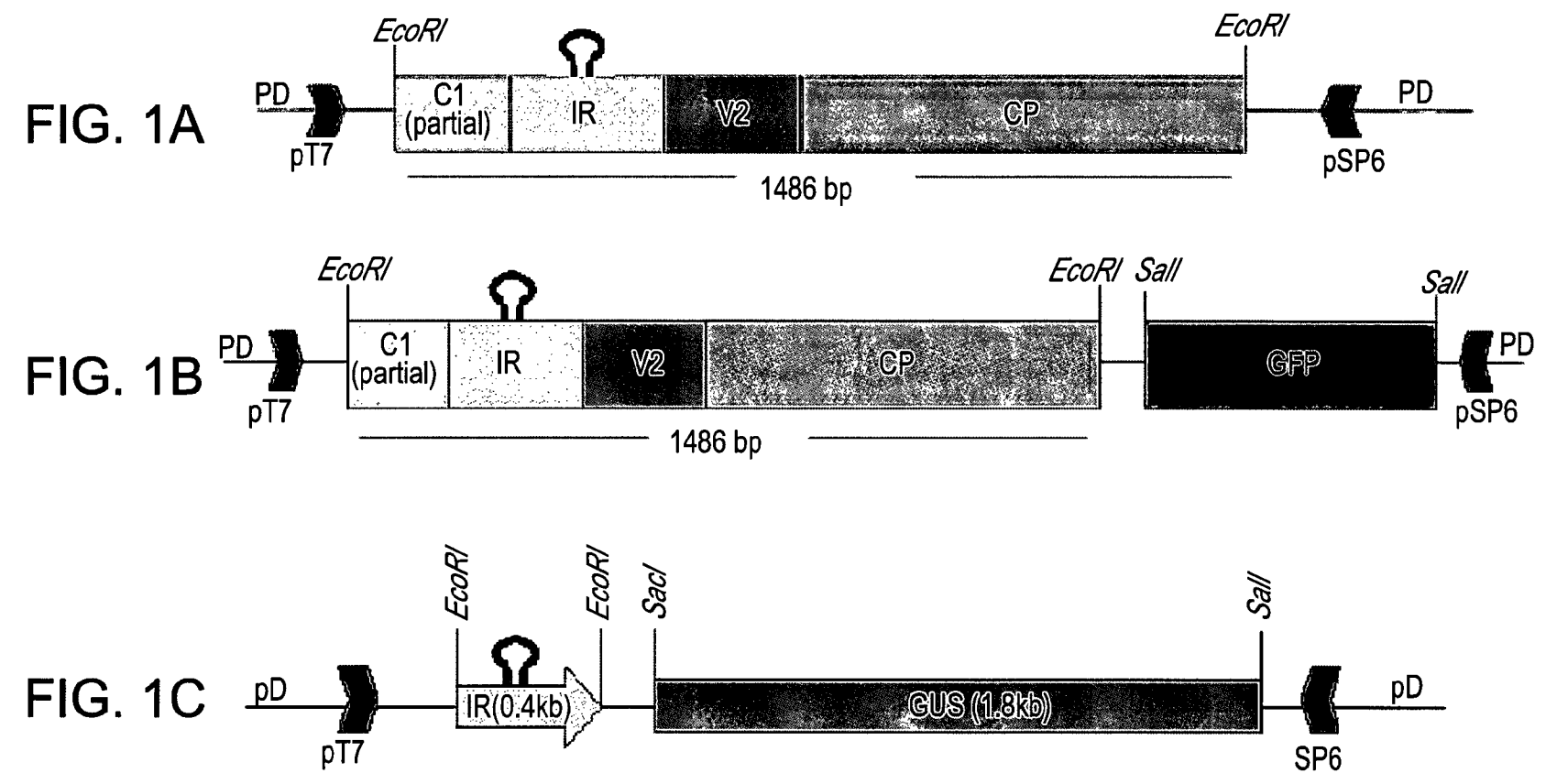

An exemplary construct of the present invention is set forth in SEQ ID NO: 11, comprising an IR region, a V2 gene and a CP gene only (see FIG. 1A). It will be appreciated that the construct may also comprise additional sequences which do not encode functional polypeptides. Accordingly, another exemplary construct of the present invention as set forth in SEQ ID NO: 10.

As is further detailed in the Examples section which follows, the above described construct can be carried out using molecular techniques such as PCR which are well known to the ordinary skilled artisan.

Preferably, the nucleic acid construct of the present invention carries one or more polynucleotide insertions so as to provide additional features to the nucleic acid construct of the present invention. Such an insertion can be several nucleotides, to several thousand nucleotides long. The insert can include a complete eukaryotic or prokaryotic expression vector a polylinker insert or a molecule having a biological activity. In any case, it should be noted that the nucleic acid construct of the present invention can carry inserts which increase the final geminivirus by 20-100% and as much as 200% beyond that of a wild type genome and yet, the nucleic acid construct of the present invention is capable of efficiently spreading throughout the host plant. The insert can encode alternative or additional functions including for example, bacterial replication, antibiotic resistance, affinity purification tags and the like.

One preferred use for the nucleic acid constructs of the present invention is plant expression of a polynucleotide or a polypeptide of interest. The polynucleotide which encodes the molecule of interest may be inserted into the expression construct described herein, wherein the IR region of the construct serves as a promoter therefore—see for example FIG. 1B. Alternatively, the polynucleotide encoding the molecule of interest may be inserted on an additional construct which only comprises an IR sequence (i.e. a transactivatable expression vector). This set up may be particularly useful for expression of a dsRNA capable of down-regulating expression of a gene. Since the IR region acts as a bidirectional promoter, an IR region may be flanked on both sides by a polynucleotide sequence encoding RNA molecules, which following expression are capable of hybridizing to form a dsRNA. This set up is described in more detail herein below and in WO2007/141790, incorporated herein by reference.

Co-administration of the transactivatable expression vector together with the construct of the present invention would result in expression of the molecule of interest (see for example FIGS. 3A-B). Alternatively, the transactivation can be effected by stepwise introduction of the construct of the present invention and the transactivatable expression vector.

One of ordinary skill in the art is familiar with nucleic acids or proteins whose expression, controlled by the expression vector of the present invention, is advantageous. Furthermore, the skilled artisan is familiar with genes whose repression or deletion, by means of expression of, for example, a suitable double-stranded RNA, or an antisense RNA, would lead to a desired effect.

Nucleic acid sequences whose expression under the control of the expression vector of the present invention has advantageous effects are exemplified below.

The expressed polynucleotide sequence can encode a molecule which would protect the plant from abiotic stress factors such as drought, heat or chill. Examples include antifreeze polypeptides from *Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

The expressed polynucleotide sequence could be a metabolic enzyme for use in the food-and-feed sector. Examples include, phytases (GenBank Acc. No.: A19451) and cellulases.

The expressed polynucleotide sequence can confer resistance to viruses, fungi, insects, nematodes and diseases, by directly attacking the pathogen, turning on the host defenses or by leading to an accumulation of certain metabolites or proteins. Examples of include glucosinolates (defense against herbivores), chitinases or glucanases and other enzymes which destroy the cell wall of parasites, ribosome-inactivating proteins (RIPS) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, α-amylase inhibitor or protease inhibitors (cowpea trypsin inhibitor), lectins such as wheatgerm agglutinin, siRNA, antisense RNA, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents thereof.

Accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77).

The expression of synthetic cryIA(b) and cryIA(c) genes, which encode *lepidoptera*-specific *Bacillus thuringiensis* delta-endotoxins can bring about a resistance to insect pests in various plants (Goyal R K et al. (2000) Crop Protection 19(5):307-312).

Additional genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

The expressed polynucleotide sequence can bring about an accumulation of chemicals such as of tocopherols, tocotrienols or carotenoids. One example of such a polynucleotide is phytoene desaturase. Preferred are nucleic acids which encode the *Narcissus pseudonarcissus* photoene desaturase (GenBank Acc. No.: X78815) or functional equivalents thereof.

The expressed polynucleotide sequence can be used for production of nutraceuticals such as, for example, polyunsaturated fatty acids (arachidonic acid, eicosapentaenoic acid or docosahexaenoic acid) examples include, fatty acid elongases and/or desaturases, or for production of proteins with improved nutritional value such as, for example, with a high content of essential amino acids (for example the high-methionine 2S albumin gene of the brazil nut). Preferred are polynucleotide sequence which encode the *Bertholletia excelsa* high-methionine 2S albumin (GenBank Acc. No.: AB044391), the *Physcomitrella patens* delta6-acyl-lipid desaturase (GenBank Acc. No.: AJ222980; Girke et al. (1998) Plant J 15:39-48), the *Mortierella* alpina delta6-desaturase (Sakuradani et al. 1999 Gene 238:445-453), the *Caenorhabditis elegans* delta5-desaturase (Michaelson et al. 1998, FEBS Letters 439:215-218), the *Caenorhabditis elegans* A5-fatty acid desaturase (des-5) (GenBank Acc. No.: AF078796), the *Mortierella alpina* delta5-desaturase (Michaelson et al. JBC 273:19055-19059), the *Caenorhabditis elegans* delta6-elongase (Beaudoin et al. 2000, PNAS 97:6421-6426), the *Physcomitrella patens* delta6-elongase (Zank et al. 2000, Biochemical Society Transactions 28:654-657), or functional equivalents of these.

The expressed polynucleotide sequence can be used for production of high-quality proteins and enzymes for industrial purposes (for example enzymes, such as lipases) or as pharmaceuticals (such as, for example, antibodies, blood clotting factors, interferons, lymphokines, colony stimulation factor, plasminogen activators, hormones or vaccines, as described by Hood E E, Jilka J M (1999) Curr Opin Biotechnol 10(4):382-6; Ma J K, Vine N D (1999) Curr Top Microbiol Immunol 236:275-92). For example, it has been possible to produce recombinant avidin from chicken albumen and bacterial P-glucuronidase (GUS) on a large scale in transgenic maize plants (Hood et al. (1999) Adv Exp Med Biol 464:127-47. Review).

The expressed polynucleotide sequence can be used for obtaining an increased storability in cells which normally comprise fewer storage proteins or storage lipids, with the purpose of increasing the yield of these substances. Examples include, acetyl-CoA carboxylase. Preferred polynucleotide sequence are those which encode the *Medicago sativa* acetyl-CoA carboxylase (accase) (GenBank Acc. No.: L25042), or functional equivalents thereof.

Additional examples of expressible polynucleotides include Hepatitis B surface antigen [Kumar G B S et al., PLANTA 222 (3): 484-493, 2005], herbicide resistance [Duke, S O, *Pest Management Science* 61:211-218, 2005], interferon [Edelbaum, O. et al., *J. Interferon Res.* 12: 449-453, 1992], T7-RNA polymerase [Zeitoune et al., *Plant Science* 141:59-65, 1997].

Further examples of polynucleotide sequence which can be expressed by the expression vector of the present invention are mentioned for example in Dunwell J M, Transgenic approaches to crop improvement, J Exp Bot. 2000; 51 pages 487-96.

The expression vector of the present invention can also be employed for the reduction (suppression) of transcription and/or translation of target genes. Thus, the expression vector of the present invention can express nucleic acids which bring about PTGS (post transcriptional gene silencing) or TGS (transcriptional silencing) effects and thus a reduction of the expression of endogenous genes. Such reduction can be achieved for example by expression of an antisense RNA (EP-A1 0 458 367; EP-A1 0 140 308; van der Krol A R et al. (1988) BioTechniques 6(10):658-676; de Lange P et al. (1995) Curr Top Microbiol Immunol 197:57-75, inter alia) or of a double-stranded RNA, each of which has homology with the endogenous target gene to be suppressed. Also, the expression of a suitable sense RNA can bring about a reduction of the expression of endogenous genes, by means of what is known as co-suppression (EP-A1 0 465 572). Especially preferred is the expression of a double-stranded small interfering RNA (siRNA) for reducing the gene expression of a target gene via RNA interference (RNAi). WO 99/32619 and WO 99/53050 describe methods for inhibiting individual target genes using an RNA with double-stranded structure, where the target gene and the region of the RNA duplex have at least partial identity (see also: Montgomery M K et al. (1998) Proc Natl Acad Sci USA 95:15502-15507; Sharp P A (1999) Genes & Development 13(2):139-141; Fire A et al. (1998) Nature 391:806-11).

The following exemplifies applications where reduction of gene expression can be employed using the expression vector of the present invention.

Delayed fruit maturation or a modified maturation phenotype (prolonged maturation, later senescence) can be achieved for example by reducing the gene expression of genes selected from the group consisting of polygalacturonases, pectin esterases, beta.-(1,4)glucanases (cellulases), beta.-galactanases (.beta.-galactosidases), or genes of ethylene biosynthesis, such as 1-aminocyclopropane-1-carboxylate synthase, adenosylmethionine hydrolase (SAMase), aminocyclopropane-1-carboxylate deaminase, aminocyclopropane-1-carboxylate oxidase, genes of carotenoid biosynthesis such as, for example, genes of pre-phytoene biosynthesis or phytoene biosynthesis, for example phytoene desaturases, and O-methyltransferases, acyl carrier protein (ACP), elongation factor, auxin-induced gene, cysteine(thiol) proteinases, starch phosphorylases, pyruvate decarboxylases, chalcone reductases, protein kinases, auxin-related gene, sucrose transporters, meristem pattern gene. Further advantageous genes are described for example in WO 91/16440, WO 91/05865, WO 91/16426, WO 92/17596, WO 93/07275 or WO 92/04456. Especially preferred is the reduction of the expression of polygalacturonase for the prevention of cell degradation and mushiness of plants and fruits, for example tomatoes. Nucleic acid sequences such as that of the tomato polygalacturonase gene (GenBank Acc. No.: x14074) or its homologs are preferably used for this purpose.

Improved protection against abiotic stress factors (heat, chill, drought, elevated moisture, pollutants, UV radiation). It is preferred to reduce the expression of genes which are implicated in stress reactions.

The reduction of the gene expression of genes encoding storage proteins (hereinbelow SPs) has numerous advantages, such as, for example, the reduction of the allergenic potential or modification regarding composition or quantity of other metabolites, such as, for example, oil or starch content.

Resistance to plant pathogens such as arachnids, fungi, insects, nematodes, protozoans, viruses, bacteria and diseases can be achieved by reducing the gene expression of genes which are essential for the growth, survival, certain developmental stages (for example pupation) or the multiplication of a specific pathogen. Such a reduction can bring about a complete inhibition of the abovementioned steps, or else a delay of same. They can take the form of plant genes which for example make possible the penetration of the pathogen, but may also be homologous pathogen genes. The transgenically expressed nucleic acid sequence (for example the double-stranded RNA) is preferably directed against genes of the pathogen. The antipathogenic agent which acts may be, in this context, the transgenically expressed nucleic acid sequence itself (for example the double-stranded RNA), but also the transgenic expression cassettes or transgenic organisms. The plants themselves, in the form of a transgenic organism, may contain the agents and pass them on to the pathogens, for example in the form of a stomach poison. Various essential genes of a variety of pathogens are known to the skilled artisan (for example for nematode resistance WO 93/10251, WO 94/17194).

Virus resistance can be achieved for example by reducing the expression of a viral coat protein, a viral replicase, a viral protease and the like. A large number of plant viruses and suitable target genes are known to the skilled artisan.

Reduction of undesired, allergenic or toxic plant constituents such as, for example, glucosinolates or patatin. Suitable target genes are described (in WO 97/16559, inter alia). The target genes which are preferred for reduction of allergenic proteins are described for example by Tada Y et al. (1996) FEBS Lett 391(3):341-345 or Nakamura R (1996) Biosci Biotechnol Biochem 60(8):1215-1221.

Delayed signs of senescence. Suitable target genes are, inter alia, cinnamoyl-CoA:NADPH reductases or cinnamoyl-alcohol dehydrogenases. Further target genes are described (in WO 95/07993, inter alia).

Reduction of the susceptibility to bruising of, for example, potatoes by reducing for example polyphenol oxidase (WO 94/03607) and the like.

Increase of the methionine content by reducing threonine biosynthesis, for example by reducing the expression of threonine synthase (Zeh M et al. (2001) Plant Physiol 127(3): 792-802).

It will be appreciated that the nucleic acid construct of the present invention can also express homologues of the above described molecules that exhibit the desired activity (i.e., the biological activity). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, identical to any of the expressed sequences described above as determined using the BestFit software of the Wisconsin sequence analysis package, utilizing the Smith and Waterman algorithm, where gap weight equals 50, length weight equals 3, average match equals 10, and average mismatch equals $-9$.

Thus, the present invention provides a geminivirus based nucleic acid construct which spreads systemically throughout the host plant and yet does not induce symptoms therein.

In summary, the nucleic acid construct of the present invention can be utilized for any purpose. Examples of uses include the following:

(i) plant expression of proteins (specific examples provided hereinabove) for various purposes including plant improvement, biopharming etc;

(ii) plant expression of nucleic acid molecules (e.g. siRNA, specific examples provided hereinabove);

(iii) produce indicator plants which detect viral infection—a plant carrying a construct including a reporter molecule (e.g. fluorophore) attached to the IR region would express the reporter in when infected by a geminivirus; and (iv) produce infection-resistant plants—a plant carrying a construct including an anti-viral or anti-plant molecule attached, for example, to the IR region would express such a molecule when infected by a geminivirus; such "immunity" or suicide scheme would only be active when the plant is infected; since the nucleic acid constructs of the present invention are preferably transient and not stably integrated into a genome of the host plant, such a trait would not be inherited by the progeny of the plant nor would it persist in commercial products of the plant.

The nucleic acid construct of the present invention can be utilized to stably or preferably transiently transform plant cells. In stable transformation, the nucleic acid molecule of the present invention is integrated into the plant genome, and as such it represents a stable and inherited trait. In transient transformation, the nucleic acid molecule is expressed by the cell transformed but not integrated into the genome, and as such represents a transient trait.

There are various methods of introducing foreign genes into both monocotyledonous and dicotyledonous plants (Potrykus, I. (1991). Annu Rev Plant Physiol Plant Mol Biol 42, 205-225; Shimamoto, K. et al. (1989). Fertile transgenic rice plants regenerated from transformed protoplasts. Nature (1989) 338, 274-276).

The principal methods of the stable integration of exogenous DNA into plant genomic DNA includes two main approaches:

(i) *Agrobacterium*-mediated gene transfer. See: Klee, H. J. et al. (1987). Annu Rev Plant Physiol 38, 467-486; Klee, H. J. and Rogers, S. G. (1989). Cell Culture and Somatic Cell Genetics of Plants, Vol. 6, Molecular Biology of Plant Nuclear Genes, pp. 2-25, J. Schell and L. K. Vasil, eds., Academic Publishers, San Diego, Cal.; and Gatenby, A. A. (1989). Regulation and Expression of Plant Genes in Microorganisms, pp. 93-112, Plant Biotechnology, S. Kung and C. J. Arntzen, eds., Butterworth Publishers, Boston, Mass.

(ii) Direct DNA uptake. See, e.g.: Paszkowski, J. et al. (1989). Cell Culture and Somatic Cell Genetics of Plants, Vol. 6, Molecular Biology of Plant Nuclear Genes, pp. 52-68, J. Schell and L. K. Vasil, eds., Academic Publishers, San Diego, Cal.; and Toriyama, K. et al. (1988). Bio/Technol 6, 1072-1074 (methods for direct uptake of DNA into protoplasts). See also: Zhang et al. (1988). Plant Cell Rep 7, 379-384; and Fromm, M. E. et al. (1986). Stable transformation of maize after gene transfer by electroporation. Nature 319, 791-793 (DNA uptake induced by brief electric shock of plant cells). See also: Klein et al. (1988). Bio/Technology 6, 559-563; McCabe, D. E. et al. (1988). Stable transformation of soybean (*Glycine max*) by particle acceleration. Bio/Technology 6, 923-926; and Sanford, J. C. (1990). Biolistic plant transformation. Physiol Plant 79, 206-209 (DNA injection into plant cells or tissues by particle bombardment). See also: Neuhaus, J. M. et al. (1987). Theor Appl Genet. 75, 30-36; and Neuhaus, J. M. and Spangenberg, G. C. (1990). Physiol Plant 79, 213-217 (use of micropipette systems). See U.S. Pat. No. 5,464,765 (glass fibers or silicon carbide whisker transformation of cell cultures, embryos or callus tissue). See also: DeWet, J. M. J. et al. (1985). "Exogenous gene transfer in maize (*Zea mays*) using DNA-treated pollen," Experimental Manipulation of Ovule Tissue, G. P. Chapman et al., eds., Longman, New York-London, pp. 197-209; and Ohta, Y. (1986). High-Efficiency Genetic Transformation of Maize by a Mixture of Pollen and Exogenous DNA. Proc Natl Acad Sci USA 83, 715-719 (direct incubation of DNA with germinating pollen).

The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch, R. B. et al. (1988). "Leaf disc transformation." Plant Molecular Biology Manual A5, 1-9, Kluwer Academic Publishers, Dordrecht). A supplementary approach employs the *Agrobacterium* delivery system in combination with vacuum infiltration. The *Agrobacterium* system is especially useful for in the creation of transgenic dicotyledenous plants.

There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues. Additional direct DNA transfer techniques include glass or silicone carbide whiskers (see, for example, Dunwell, Methods Mol. Biol. 1999; 111:375-82).

Following stable transformation, plant propagation then occurs. The most common method of plant propagation is by seed. The disadvantage of regeneration by seed propagation, however, is the lack of uniformity in the crop due to heterozygosity, since seeds are produced by plants according to the genetic variances governed by Mendelian rules. In other words, each seed is genetically different and each will grow with its own specific traits. Therefore, it is preferred that the regeneration be effected such that the regenerated plant has identical traits and characteristics to those of the parent transgenic plant. The preferred method of regenerating a transformed plant is by micropropagation, which provides a rapid, consistent reproduction of the transformed plants.

Micropropagation is a process of growing second-generation plants from a single tissue sample excised from a selected parent plant or cultivar. This process permits the mass reproduction of plants having the preferred tissue and expressing a fusion protein. The newly generated plants are genetically identical to, and have all of the characteristics of, the original plant. Micropropagation allows for mass production of quality plant material in a short period of time and offers a rapid multiplication of selected cultivars with preservation of the characteristics of the original transgenic or transformed plant. The advantages of this method of plant cloning include the speed of plant multiplication and the quality and uniformity of the plants produced.

Micropropagation is a multi-stage procedure that requires alteration of culture medium or growth conditions between stages. The micropropagation process involves four basic stages: stage one, initial tissue culturing; stage two, tissue culture multiplication; stage three, differentiation and plant formation; and stage four, greenhouse culturing and hardening. During stage one, the tissue culture is established and certified contaminant-free. During stage two, the initial tissue culture is multiplied until a sufficient number of tissue samples are produced to meet production goals. During stage three, the newly grown tissue samples are divided and grown into individual plantlets. At stage four, the transformed plantlets are transferred to a greenhouse for hardening where the plants' tolerance to light is gradually increased so that they can continue to grow in the natural environment.

Transient transformation of, for example, leaf cells, meristematic cells, or the whole plant is also envisaged by the present invention.

Transient transformation can be effected by any of the direct DNA transfer methods described above or by mechanical or vector mediated viral infection using the plant viruses derived plasmid of the present invention.

As mentioned, the constructs of the present invention may also be transformed into a plant via grafting a section of one plant which comprises the construct onto a section of another plant. Alternatively, the constructs of the present invention may be transformed into a plant by soaking its roots into a solution comprising the construct.

Thus, according to another aspect of the present invention there is provided a method of expressing a molecule of interest in a plant, the method comprising contacting roots of the plant in a solution comprising at least one Geminivirus based expression construct so as to allow the at least one Geminivirus based expression construct to be absorbed by the roots, the expression construct comprising a polynucleotide encoding the molecule of interest, and further the expression construct being capable of systemic symptomless spread in a plant host, thereby expressing a molecule of interest in a plant.

According to yet another aspect of the present invention there is provided a method of expressing a molecule of interest in a plant, the method comprising grafting a section of a first plant infected with at least one Geminivirus based expression construct onto a section of a second plant, the expression construct comprising a polynucleotide sequence which encodes the molecule of interest, and further the Geminivirus based expression construct being capable of systemic symptomless spread in a plant host, thereby expressing a molecule of interest in a plant.

As used herein, the term "grafting" refers to the joining together of the parts of plants so that they bind together and the sap can flow, thus forming a new plant that can grow and develop. A graft therefore consists of two parts: (i) the lower part is the rootstock as referred to herein and essentially consists of the root system and a portion of the stem, and (ii) the upper part, the scion or graft, which gives rise to the aerial parts of the plant. It will be appreciated that a single graft can comprise two parts of the same plant of alternatively a single graft can comprise parts of two different plants.

Preferably, the first plant and the second plant are compatible for grafting.

As used herein, the term "compatible" refers to the ability of the grafted rootstock and plant tissue to grow together and survive. It is well known that compatible rootstock and plant tissue grafts do not have to be from the same plant species. For example, tomato scions can be grafted onto eggplant rootstock. Transgenic rootstock can be prepared using standard methods.

Grafting can be accomplished using standard materials and methods known in the art. (See, for example, Black et al. (2003); Fernandez-Garcia et al. (2004); Edelstein et al. (2004); see Worldwide Website: wwwdotparamount-seedsdotcom/Paramountonline/graftingdothtm; see Worldwide Website: wwwdotagnetdotorg/library/article/eb480dothtml).

Exemplary plants which can be grafted according to this aspect of the present invention include dicotyledonous plants, such as, for example, peas, alfalfa, tomato, tomatillo, melon, chickpea, chicory, clover, kale, lentil, soybean, tobacco, potato, sweet potato, radish, cabbage, rape, apple trees, grape, cotton, sunflower, citrus (including orange, mandarin, kumquat, lemon, lime, grapefruit, tangerine, tangelo, citron, and pomelo), pepper, bean, and lettuce. Plants within the scope of the present invention also include conifers.

Examples of tomato rootstock that can be used to prepare pathogen resistant transgenic rootstock includes, but is not limited to, "PG3" and "Beaufort." Examples of tomato cultivars that can be used to provide scions for the present invention include, but are not limited to, "Monroe," "Belle," Summer Set," "Match," Trust," "Better Boy," "Celebrity," "Grace," "Heinz 1439," "Roma," "Rugers," "Ultra Girl," "2710," "BHN 665," "STM 0227," "STM 5206," "Boy oh Boy," "Jubilation," "Sunchief," and "Fabulous."

Contemplated geminivirus based expression constructs that may be grafted from one plant to another or soaked up by plant roots are those described herein above and further those described in International Patent Application WO2007/141790.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Methods and Materials

Cloning of TYLCV—

A full 2.8-genome-length clone of the Israeli strain of TYLCV (SEQ ID NO: 4 GenBank accession # X15656) was produced as described in Navot, N., et al [Virology 185, 151-161 (1991)].

Construction of IL-60—

The IL-60 vector (SEQ ID NO: 2) of the present invention was constructed by making the following changes to the native TYLCV viral vector (SEQ ID NO: 4):

(i) a deletion of a stretch of 60 nucleotides (nos. 552 to 612 of SEQ ID NO: 1) encoding 20 amino acids near the N-terminus of the coat protein, TYLCV-CP (nos. 27 to 46 of SEQ ID NO: 5). Deletion was carried out by inverse PCR in accordance with Livneh, O. et al. [Euphytica 62:97-102 (1992)] using primers directed outward from the ends of the deleted segment [Inverse forward primer (unphosphorylated): OH-acaggcccatagaccgaaagccca; SEQ ID NO: 14, Inverse reverse (phosphorylated): P-tgggctgtcgaagttcagcct; SEQ ID NO: 15]. The self-ligated PCR product was cleaved with SacI to produced a single (linear) product, confirming that a circular form has been made (non-ligated, linear PCR products would have produced two fragments upon cleaving).

(ii) a PCR derived deletion of T in position 640 (of TYLCV) and addition of G at following position 744 thereby generating a frame shift in the TYLCV sequence (SEQ ID NO: 4) encoding positions 56-91 of native TYLCV-CP protein (SEQ ID NO: 5). Frame shift was achieved in 2 steps, first aimed at deleting the T and second at adding the G. The first step aimed at deleting the T at position 640 included two PCR steps, an initial and nested PCR. The initial PCR product was cut with TaqI, and a mutated (missing the T) nested PCR product, which was situated between 2 TaqI restriction sites, was ligated instead of the cut out piece. Initial PCR amplified a 439 bp product flanked with TaqI restriction sites, and possessing two middle TaqI restriction sites. [forward primer: ggctgaacttcgacagcccatacagcagccgtgctgctg (SEQ ID NO: 20), BcefI recognition site is emphasized in bold, TaqI restriction site is underlined; reverse primer: gcggtactgggctcattata tcgaacatatt (SEQ ID NO: 21), BmrI recognition site is emphasized in bold, TaqI restriction sites is underlined]. Nested PCR amplified a product flanked by the same TaqI restriction site at the forward end (using the same forward primer-SEQ ID NO: 20) and another middle TaqI restriction site at the reverse end. The reverse primer also possessed the missing respective T [nested reverse primer: ggcttcgatacattctgtat↑ttctg (SEQ ID NO: 22), TaqI recognition site is emphasized in bold, arrow represents the position of the deleted T]. The initial PCR product was cleaved with TaqI and run on a gel, to obtain 3 bands (from the 2 flanking and 2 middle TaqI restriction sites). The upstream piece, situated between the primers of the nested PCR, was removed. The remaining 2 bands were extracted from the gel and ligated to the mutated PCR product of the nested PCR to obtain the desired sequence (BcfI to TaqI with a missing T). The second step, aimed at adding the G at position 744, involved an initial PCR with primers holding BstDSI (forward) and MaeIII (reverse) restriction sites [forward primer: ctgatgttccccgtggatgt-gaaggcccat (SEQ ID NO: 23), BstDSI recognition site is emphasized in bold; reverse primer: ccacgagtaacatcactaa-caacCaacaatac (SEQ ID NO: 24), MaeIII recognition site is emphasized in bold, added G (C in the reverse complement) is also emphasized in bold], to obtain a PCR product holding the additional G. The PCR product, and the product of the first step (BcfI to TaqI with a missing T) were cleaved with BstDSI and MaeIII, and the cleavage product was replaced with the construct was extracted using standard procedures. IR-V2-CP was administered directly into plants, without mediation by *Agrobacterium*. The stem, or leaf petiole, of the recipient plant was punctured by a hypodermic needle. A capillary tube was inserted into the resultant hole, and approximately 2 microgram of DNA (in 100 µl of 5 mM Tris-HCl; pH 8.5) were pipetted into the capillary tube until fully soaked by the plant.

RT-PCR Analysis:

RT-PCR analysis was carried out according to standard procedures (Sambrook and Russel, 2001). Primers used for analyzing expression of IR-V2-CP-GFP are set forth in Table 1.

TABLE 1

| SEQ ID NO: | Primer design | Sequence 5'-3' | Description |
|---|---|---|---|
| SEQ ID NO: 16 | Forward | attgggctgtttccatagggc | For detection of CP (V1) |
| SEQ ID NO: 17 | Reverse | gaaggctgaacttcgacag | For detection of CP (V1) |
| SEQ ID NO: 18 | Forward | tgtgtggacaggtaatgg | For detection of GFP |
| SEQ ID NO: 19 | Reverse | ggccgaattcagtaaaggagaag | For detection of GFP |

PCR product including the added G, by ligation. Finally, IL-60 was cleaved with BceFI and BmrI, a fragment was removed and replaced by the sequence obtained in the steps described above (BcfI to BmrI with a missing T and an added G).

iii) a deletion of 45 amino acids at the C terminus of native TYLCV V2 ("pre-coat"-SEQ ID NO: 6), caused by the deletion of the TYLCV CP described hereinabove.

Construction of IL-60-BS— the IL-60-BS vector (SEQ ID NO: 1) of the present invention was constructed by ligating a linearized (Sac I) Bluescript II-KS+ plasmid (Stratagene, La Jolla, Calif., USA) into position 2443 of the IL-60 plasmid (SEQ ID NO: 2), interrupting the rep (rolling circle replication) protein (SEQ ID NO: 7) at position 93, within the N-terminus. The gene coding for C4 (symptom expression) was also interrupted by the BS insertion.

Construction of IR-GUS-pD—

The IR-GUS-pD vector (SEQ ID NO: 13) was constructed by amplifying the IR region, pre-coat ORF and a part of the 5' UTR of the coat protein ORF- (positions 61 to 473 of TYLCV; accession # X15656) using forward primer 933: atacttggacacctaatggc (SEQ ID NO: 29) and reverse primer 934: agtcacgggcccttacaa (SEQ ID NO: 30). This fragment was termed "IR-region". IR region was T/A cloned into the plasmid pDRIVE, to produce a plasmid called IR-pD (SEQ ID NO: 12). The coding sequence of GUS (bases 1466 to 3274 of GenBank accession #M14641) (SEQ ID NO: 31) was cleaved out of a GUS-carrying plasmid with SacI and SalI and inserted into a SalI/SacI cleaved pDRIVE carrying the aforementioned IR region.

Construction of IR-PRN-pD—

The IR-PRN-pD vector was constructed by placing the entire PRN operon (as a single piece carrying all 4 genes) of *P. fluorescence* (corresponding to bases 424-6165 of GenBank accession # U74493; SEQ ID NO: 32) in place of GUS in IR-GUS-pD.

Propagation of IR-V2-CP, IR-V2-CP-GFP, IL-60 and IR-GUS-pD, and their Administration to Plants—

*E. coli* cells were transformed with the above described constructs and propagated under ampicillin selection; the Primers used in order to detect GUS were as follows: Forward: ATTGATCAGCGTTGGTGGGA (SEQ ID NO: 25); Reverse: TGCGGTCGCGAGTGAAGATC (SEQ ID NO: 26).

Primers used in order to detect PRN was as follows: Forward: GCGAACGAACACGATAGCAA (SEQ ID NO: 27); Reverse: CGTCAATGAGGGCGTGAAT (SEQ ID NO: 28).

Delivery of Plasmids to Plants by Grafting—

IL-60-BS and IR-GUS (or IR-PRN) were injected to tobacco and tomato plants as described herein above. Plants in which GUS (or PRN) have been replicated and spread (as indicated by PCR) were set aside for the following grafting experiments.

Scions of tobacco and tomato plants in which IR-GUS or IR-PRN were present, were grafted on untreated tobacco and tomato plants respectively (the rootstocks). The rootstocks were PCR analyzed for GUS and PRN one month following grafting. DNA was extracted from leaves remote from the point of grafting by at least 3 leaves.

Delivery of Plasmids to Plants by Soaking—

Roots of seedlings or young plantlets (tomato, tobacco, grapevines) were slightly trimmed. The roots were soaked in a 2-5 µg of each of IL-60-BS and IR-GUS dissolved in water. The plantlets were kept in the solution until all liquid was soaked up. Another volume of water was then added and after it has also been soaked up the plantlets were planted in pots. Replication and spread of GUS was tested periodically by PCR in upper leaves.

Example 1

IR and the Sense Viral Genes (V1 and V2) are Sufficient for Stabilization, Movement and Spread of Artificial Satellites in Plant Tissues IR-carrying satellites are activated to replicate, move and be expressed, either by a helper virus or by the mutated disarmed vector IL-60-BS (see WO2007/141790, incorporated herein by reference). The following example now shows that the sense-transcribed genes of TYLCV alone, under IR regulation, are sufficient for self-replication, movement and expression. This genomic segment can promote replication, movement and expression of IR-carrying satellites in trans as well.

Figure 2C:
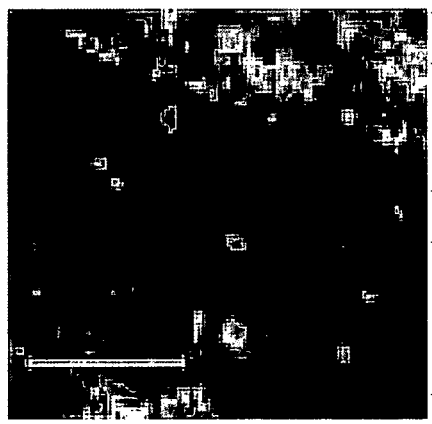
Figure 2D:
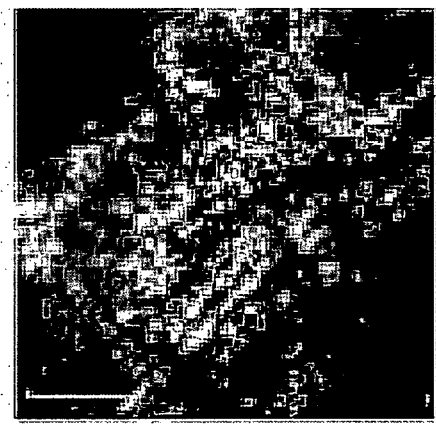
Figure 2E:
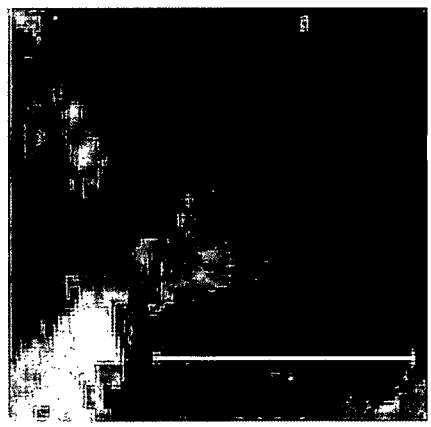
Figure 2F:
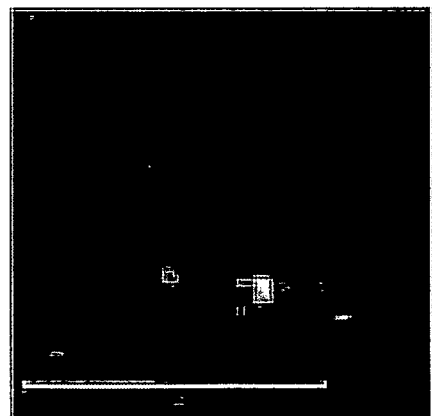

GFP was fused to the 3' end of CP in the IR-V2-CP construct (FIGS. 1A and 1B). Leaves remote from the point of injection were analyzed (FIGS. 2A-F). Upon injection into tomato plants, GFP fluorescence was observed mainly in the nuclei of phloem companion cells (FIGS. 2C-D). It was also observed at the cell periphery, suggesting movement across plasmodesmata (FIGS. 2A, E), as well as in mesophyll cells (FIGS. 2A, F).

Figures 3A, 3B, 3C, 3D, 3E, 3F:
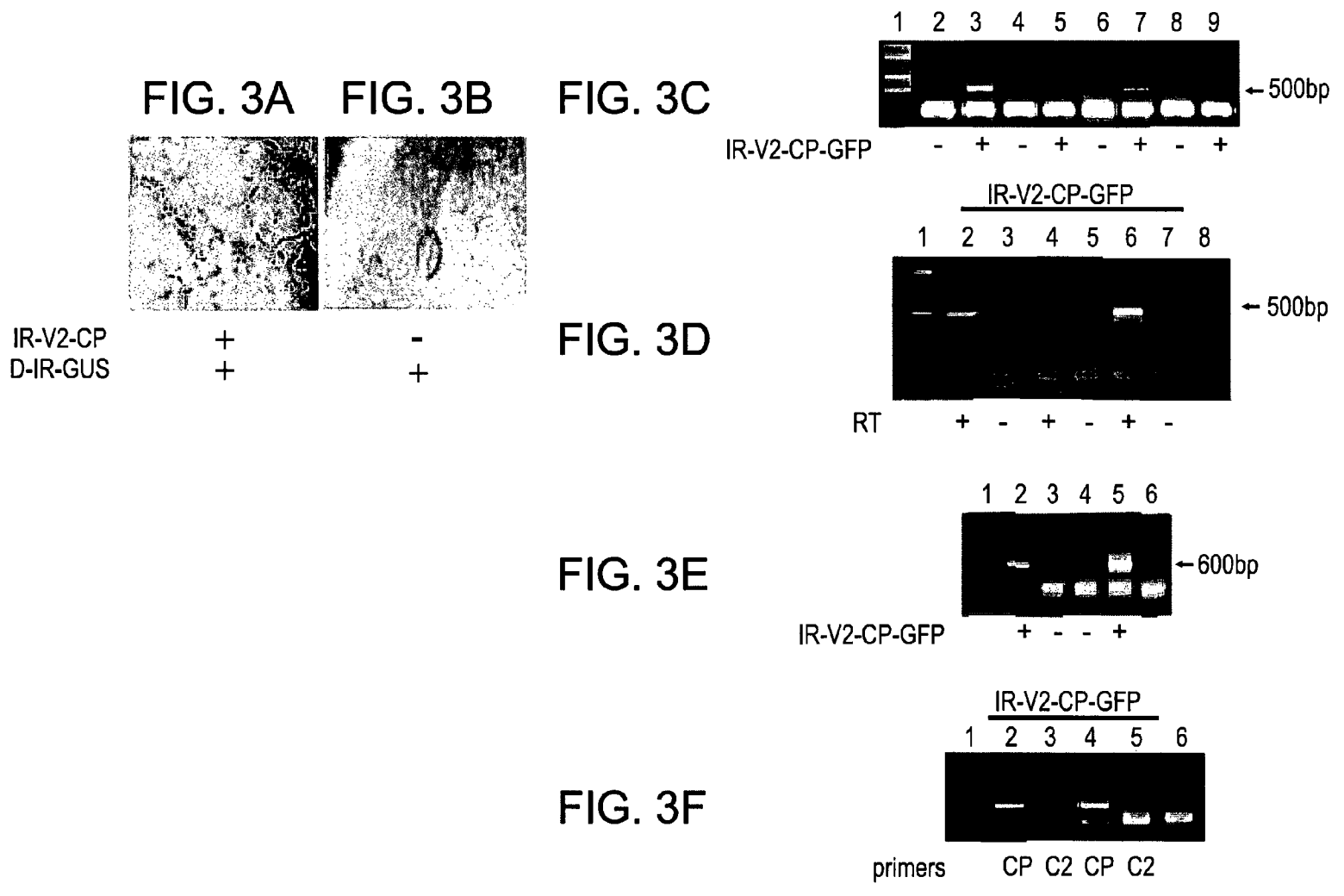

PCR analysis indicated the presence of both TYLCV CP and GFP sequences, as well as TYLCV transcripts in treated plants (FIGS. 3C-E). The absence of other TYLCV sequences (FIG. 3F) indicated that the plants were TYLCV-free. These results indicate that IR-V2-CP-GFP replicates and moves on its own. GFP was present in the nuclei of companion cells, at the cell periphery and, apparently, across plasmodesmata.

The IR-V2-CP construct can induce replication and movement of another DNA in trans, providing the DNA carries an IR. As shown in FIGS. 3A-B, the artificial satellite IR-GUS (FIG. 1C) was mobilized and expressed GUS in the presence of IR-V2-CP.

Example 2

Delivery of IL-60-BS to Plants by Grafting

Figure 5:
FIG. 5 is a photograph of an ethidium bromide stained gel demonstrating the results of PCR analysis for PRN in rootstocks which had been grafted with scions carrying IL-60-BS+IR-PRN. Lanes 1 to 3: Different grafted tobacco plants. Lanes 4 to 6: Different grafted tomato plants. Lane 7-9: Negative control (no template). Lane 10: Size markers

The results are illustrated in FIGS. 4 and 5. Specifically, these Figures illustrate that both IR-GUS (FIG. 4) and IR-PRN (FIG. 5) were transferred from the scion to the rootstock where they replicated and spread.

Example 3

Delivery of IL-60-BS by Through the Roots

Figure 6:
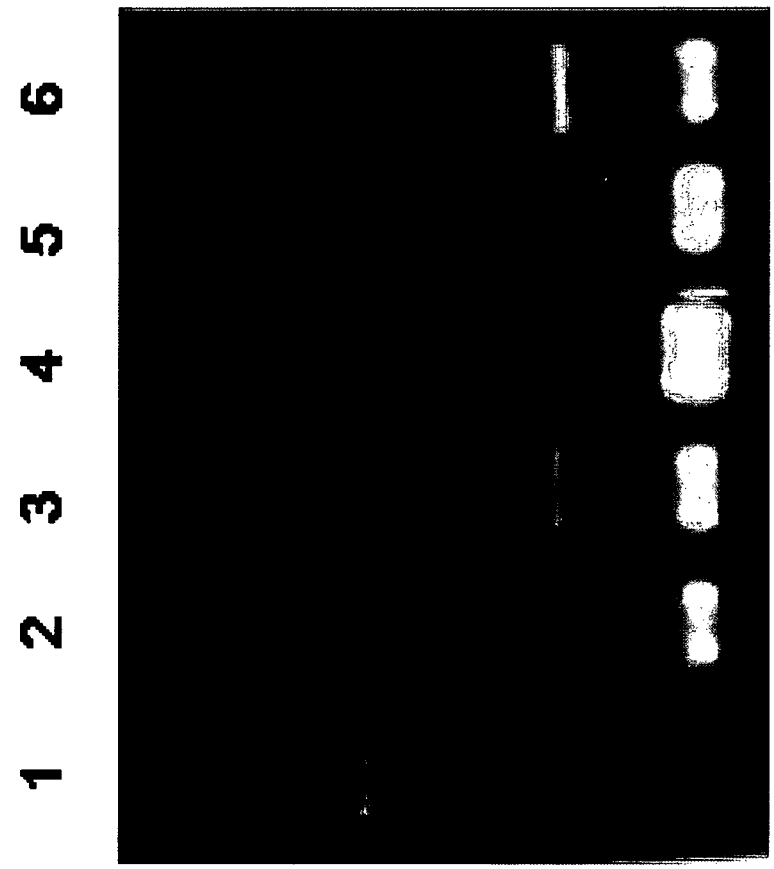
FIG. 6 is a photograph of an ethidium bromide stained gel demonstrating the results of PCR analysis for GUS from leaves of tomato plants into which IL-60-BS and IR-GUS had been transferred through the roots.

FIG. 6 demonstrates that IR-GUS was transferred through the roots and replicated and spread in the plants. The same result was achieved when other IR vectors (IR-GFP and IR-PRN) were transferred through the roots of additional plants including tomato, tobacco, grapevine and periwinkle (data not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A tomato yellow leaf curt virus (TYLCV) Geminivirus based expression construct, capable of systemic symptomless spread in a plant host, the expression construct being completely devoid of the TYLCV C2 and C3 coding sequence, the construct comprising:
   (i) a polynucleotide sequence encoding a Geminivirus intergenic region (IR);
   (ii) a polynucleotide sequence encoding a modification in a Geminivirus coat protein (CP), wherein said modification comprises a deletion in nucleotides encoding an N-terminal 100 amino acids, wherein said modification results in deletion in the C-terminal region of a Geminivirus V2 protein.

2. The expression construct of claim 1, further comprising a polynucleotide sequence encoding a modified replicase protein (C1), wherein said modification is a truncation resulting in a reduced capability of rolling circle, single stranded DNA replication compared to an unmodified TYLCV replicase, and further where said modification results in a non functioning C4 protein of said TYLCV.

3. The expression construct of claim 2, wherein said modified replicase protein is as set forth in SEQ ID NO: 36.

4. The expression construct of claim 1, being capable of replication in a prokaryotic cell.

5. The expression construct of claim 1, being incapable of plant to plant transmission by an insect vector.

6. The expression construct of claim 1, further comprising a heterologous polynucleotide sequence.

7. The expression construct of claim 6, wherein said heterologous polynucleotide is larger than 1 kb.

8. The expression construct of claim 6, wherein said heterologous polynucleotide is larger than 5 kb.

9. The expression construct of claim 6, wherein said heterologous polynucleotide comprises an operon.

10. The expression construct of claim 6, wherein said heterologous polynucleotide encodes a dsRNA or an antisense RNA.

11. The expression construct of claim 1, further comprising a bacterial polynucleotide sequence.

12. The expression construct of claim 1, wherein said modified Geminivirus V2 protein is as set forth in SEQ ID NO: 6.

13. The expression construct of claim 1, wherein said Geminivirus coat protein comprises an amino acid sequence is as set forth in SEQ ID NO: 3.

14. The expression construct of claim 1 comprising the polynucleotide sequence as set forth in SEQ ID NO: 10 or 11.

15. The expression construct of claim 6, wherein said heterologous polynucleotide encodes a polypeptide selected from the group consisting of a reporter molecule, an antiviral molecule, a viral moiety, an antifungal molecule, an antibacterial molecule, an insect resistance molecule, a herbicide resistance molecule, a biotic or abiotic stress tolerance molecule, a pharmaceutical molecule, a growth inducing molecule, and a growth inhibiting molecule.

16. The expression construct of claim 1, wherein the expression construct is adapted for expression in a plant host selected from the group consisting of Solanaceae, Cucurbitaceae, Umbelliferae, Liliaceae, Gramineae (Poaceae), Rosaceae, Musaceae, Vitacea, and Cruciferae.

17. A method of expressing a molecule of interest in a plant cell comprising introducing into the plant cell the expression construct of claim 15, said polypeptide being the molecule of interest, thereby expressing the molecule of interest in a plant cell.

18. The method of claim 17, wherein the plant cell is selected from the group consisting of a Solanaceae, a Cucurbitaceae, an Umbelliferae, a Liliaceae, a Gramineae (Poaceae), a Rosaceae, a Musaceae, a Vitacea and a Cruciferae cell.

19. The expression construct of claim 9, wherein said operon comprises the pyrrolnitrin (PRN) operon.

* * * * *